United States Patent
Pitcher

(10) Patent No.: US 10,426,862 B2
(45) Date of Patent: Oct. 1, 2019

(54) DIFFUSING APPARATUS AND METHODS

(71) Applicant: SPDI Holdings, Inc., Alpine, UT (US)

(72) Inventor: Stephen N. Pitcher, Alpine, UT (US)

(73) Assignee: SPDI Holdings, Inc., Alpine, UT (US)

( * ) Notice: Subject to any disclaimer, the term of this patent is extended or adjusted under 35 U.S.C. 154(b) by 132 days.

(21) Appl. No.: 15/727,238

(22) Filed: Oct. 6, 2017

(65) Prior Publication Data

US 2018/0099068 A1 Apr. 12, 2018

Related U.S. Application Data

(63) Continuation-in-part of application No. 15/287,733, filed on Oct. 6, 2016, now Pat. No. 10,034,987.

(51) Int. Cl.
*A61L 9/14* (2006.01)
*B01F 3/04* (2006.01)
(Continued)

(52) U.S. Cl.
CPC ............. *A61L 9/14* (2013.01); *A61L 9/145* (2013.01); *A61M 21/02* (2013.01); *B01F 3/04106* (2013.01); *B01F 3/04241* (2013.01); *F04B 13/02* (2013.01); *F04B 17/003* (2013.01); *F04B 23/028* (2013.01); *F04B 35/04* (2013.01); *F04B 43/046* (2013.01); *F04B 45/047* (2013.01); *F04B 53/16* (2013.01); *F04F 1/18* (2013.01);
(Continued)

(58) Field of Classification Search
CPC ..... A61M 11/02; A61L 9/145; B01F 3/04106; B01F 3/04241

USPC .......... 261/26, 30, 121.1, DIG. 88; 422/124
See application file for complete search history.

(56) References Cited

U.S. PATENT DOCUMENTS 6,645,436 B2 11/2003 Davis
7,407,118 B2 8/2008 Sevy
(Continued)

FOREIGN PATENT DOCUMENTS

CN 202566815 U 12/2012
CN 204106638 U 1/2015
(Continued)

OTHER PUBLICATIONS

Kim "International Search Report for Application No. PCT/US2017/055643" dated Jan. 11, 2018, 3 pages.
(Continued)

*Primary Examiner* — Robert A Hopkins
(74) *Attorney, Agent, or Firm* — Perry S. Clegg; Kunzler Bean & Adamson, PC

(57) ABSTRACT

Disclosed herein is a diffusing apparatus for diffusing essential oils into the air. The apparatus includes a reservoir configured to hold essential oils in an internal cavity, and a controller assembly removably coupled to the reservoir, the controller assembly including an air inlet port, a first controller, and a piezo micro air pump unit. The apparatus further includes a base removably coupled to the controller assembly, the base including a second controller, wherein the second controller is connected to the first controller. The apparatus further includes a tube in fluid connection at a first end with the micro air pump unit and extending into the reservoir, the tube providing a path for pressurized air from the micro air pump unit into the reservoir through a plurality of orifices at a second end of the tube.

21 Claims, 17 Drawing Sheets

(51) Int. Cl.

| | |
|---|---|
| *A61M 11/02* | (2006.01) |
| *F04B 17/00* | (2006.01) |
| *F04B 43/04* | (2006.01) |
| *F04B 13/02* | (2006.01) |
| *F04B 23/02* | (2006.01) |
| *F04B 35/04* | (2006.01) |
| *F04B 45/047* | (2006.01) |
| *F04B 53/16* | (2006.01) |
| *F04F 1/18* | (2006.01) |
| *A61M 21/02* | (2006.01) |
| *A61M 15/08* | (2006.01) |
| *A61M 21/00* | (2006.01) |

(52) U.S. Cl.
CPC ............ *A61M 11/02* (2013.01); *A61M 15/08* (2013.01); *A61M 2021/0022* (2013.01); *A61M 2205/8206* (2013.01)

(56) References Cited

U.S. PATENT DOCUMENTS

| | | | |
|---|---|---|---|
| 2002/0043568 A1 | 4/2002 | Hess | |
| 2002/0179643 A1* | 12/2002 | Knight | ............... A61L 9/03 222/146.2 |
| 2004/0238976 A1 | 12/2004 | Johns | |
| 2007/0138326 A1 | 6/2007 | Hu | |
| 2010/0084484 A1 | 4/2010 | Sevy | |
| 2017/0106333 A1 | 4/2017 | Zhu | |

FOREIGN PATENT DOCUMENTS

| | | |
|---|---|---|
| CN | 204972379 U | 1/2016 |
| CN | 205241636 U | 5/2016 |
| CN | 206139377 U | 5/2017 |
| CN | 206143854 U | 5/2017 |
| JP | 05-269189 A | 10/1993 |
| KR | 20-2014-0004200 U | 7/2014 |
| WO | 2011021980 A1 | 2/2011 |
| WO | 2015158970 A1 | 10/2015 |

OTHER PUBLICATIONS

Kim "Written Opinion of the International Searching Authority for Application No. PCT/US2017/055643" dated Jan. 11, 2018, 3 pages.

* cited by examiner

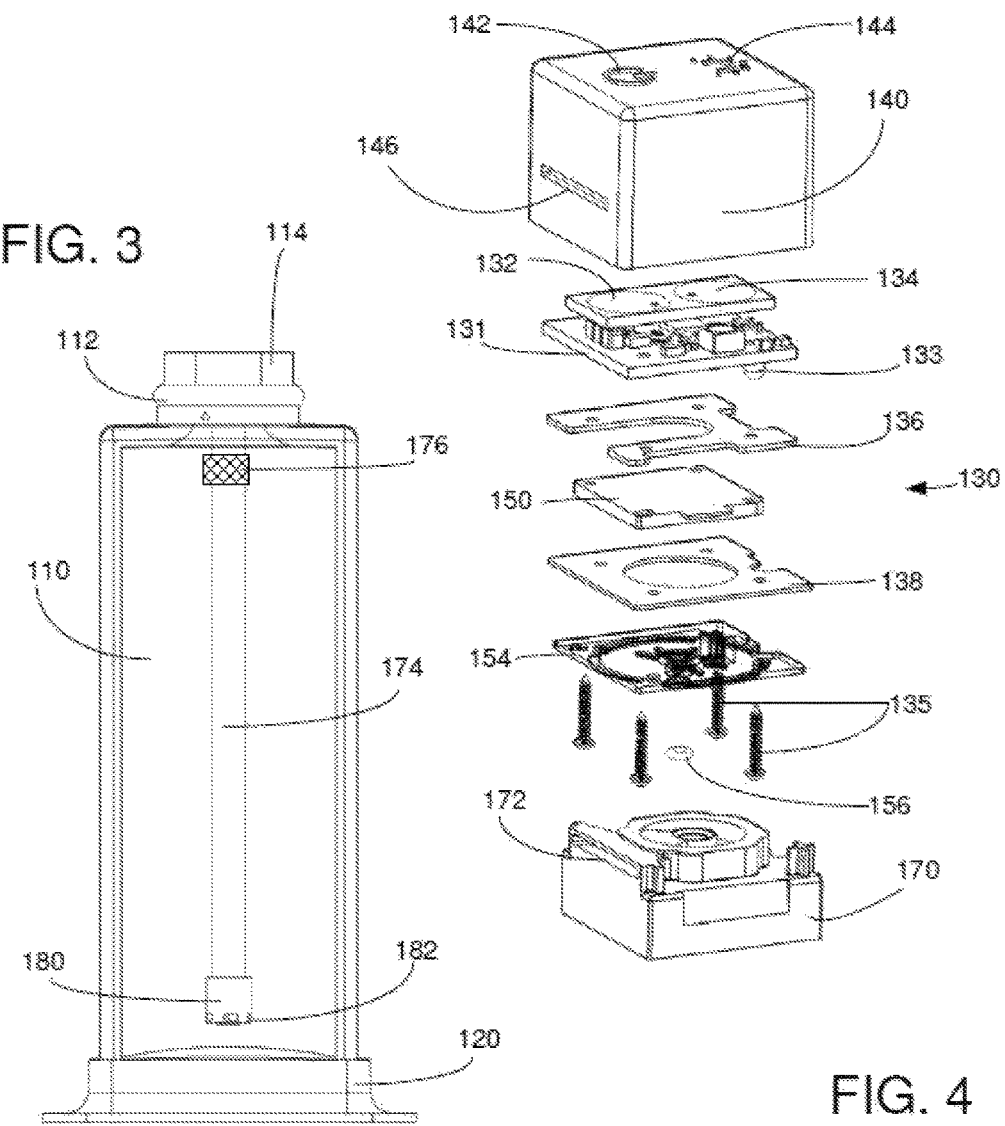

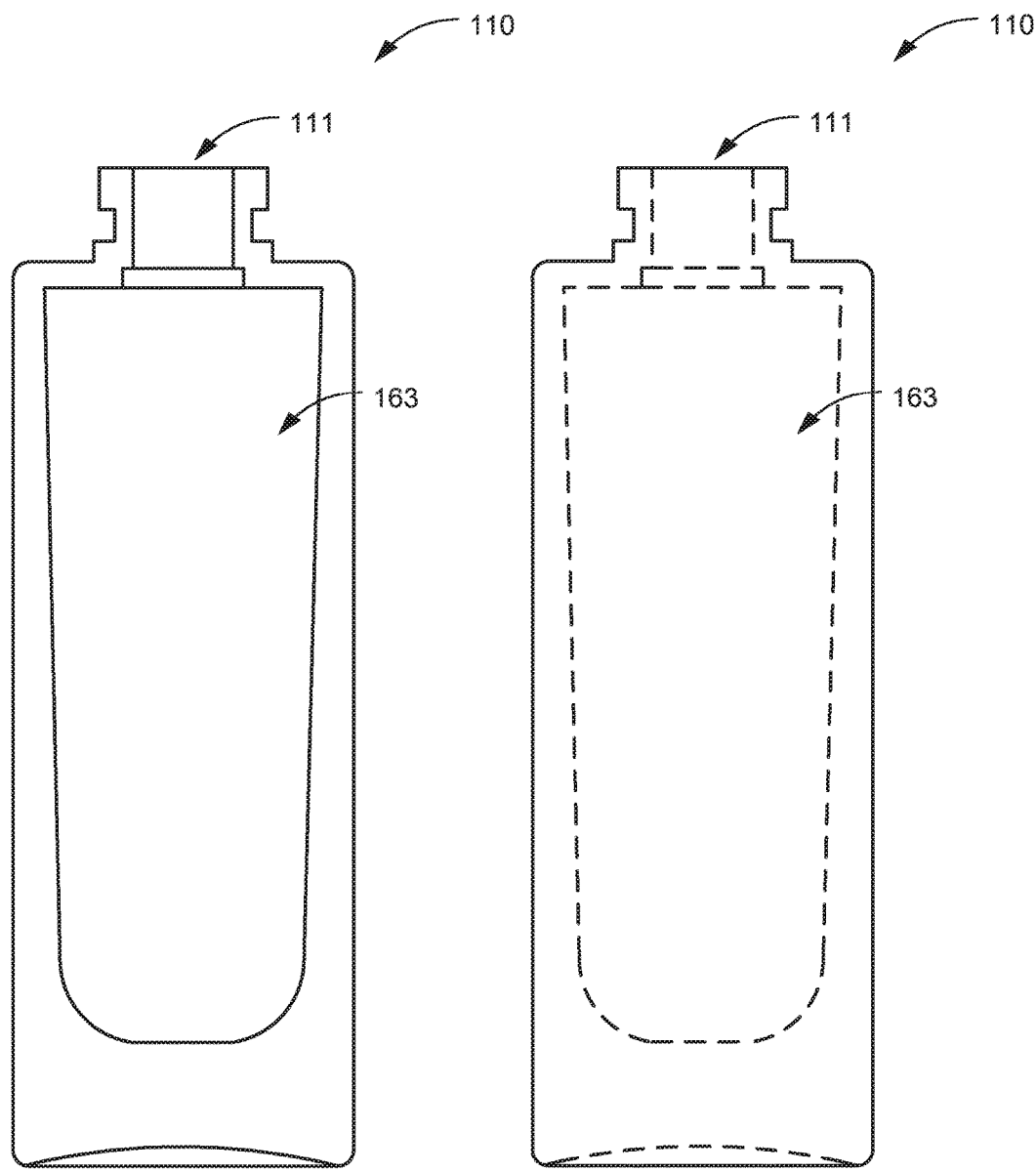

DIFFUSING APPARATUS AND METHODS

PRIORITY

This application is a continuation-in-part of U.S. patent application Ser. No. 15/287,733, filed on Oct. 6, 2016, which is incorporated by reference herein.

FIELD

This application relates generally to devices for dispersing essential oils into the air. In particular, this application relates to devices for dispersing essential oils into the air by infusing the oils with air and dispersing the saturated air.

BACKGROUND

In recent years, sales for essential oils have exploded. Essential oils are usually oils which are derived from, or include certain essential components or essences of different plant substances. Such oils are generally ingested, topically applied, or are breathed in through various methods of diffusion or atomization.

Essential oils, known as nature's living energy, are the natural, aromatic volatile liquids found in shrubs, flowers, trees, resins, fruit peels, rhizomes, roots, bushes, and seeds. The distinctive components in essential oils defend plants against insects, environmental conditions, and disease. They are also vital for a plant to grow, live, evolve, and adapt to its surroundings. Essential oils are extracted from aromatic plant sources via steam distillation, cold pressing, and other types of extraction and/or distillation. Essential oils are highly concentrated and far more potent than dry herbs. Other topically applied oils may include olive oil, almond oil, coconut oil, fatty acid oils, etc., and oils high in esters, such as jojoba oil, and waxes such as beeswax.

While essential oils often have a pleasant aroma, their chemical makeup is complex and their benefits vast—which make them much more than something that simply smells good. Essential oils are used for aromatherapy, massage therapy, emotional health, personal care, nutritional supplements, household solutions, and much more.

Diffusers for essential oils have been used to disperse the essential oils for breathing or to create a pleasant fragrance in a room or area. However, available diffusers for use with most essential oils are almost always unreliable with short service lives and high failure rate. These problems can be mitigated with meticulous care in maintaining the diffuser, which is beyond the capacity and patience of the average user.

SUMMARY

The subject matter of the present application has been developed in response to the present state of the art, and in particular, in response to the problems and disadvantages associated with conventional diffusing apparatuses and processes that have not yet been fully solved by currently available techniques. Accordingly, the subject matter of the present application has been developed to provide embodiments of a system, an apparatus, and a method that overcome at least some of the above-discussed shortcomings of prior art techniques. For example, according to one implementation, a hot drape forming process is disclosed, which facilitates consistent temperature readings throughout a part.

Disclosed herein is a diffusing apparatus for diffusing essential oils into the air according to one or more examples of the present disclosure. The apparatus includes a reservoir configured to hold essential oils in an internal cavity, and a controller assembly removably coupled to the reservoir, the controller assembly including an air inlet port, a first controller, and a micro air pump unit. The apparatus further includes a base removably coupled to the controller assembly, the base including a second controller, wherein the second controller is connected to the first controller. The apparatus further includes a tube in fluid connection at a first end with the micro air pump unit and extending into the reservoir, the tube providing a path for pressurized air from the micro air pump unit into the reservoir through a plurality of orifices at a second end of the tube. The preceding subject matter of this paragraph characterizes example 1 of the present disclosure.

The base further includes a rechargeable battery and the rechargeable battery is configured to power the first controller. The preceding subject matter of this paragraph characterizes example 2 of the present disclosure, wherein example 2 also includes the subject matter according to example 1, above.

The apparatus further includes a plurality of LEDs in the base configured to illuminate the reservoir. The preceding subject matter of this paragraph characterizes example 3 of the present disclosure, wherein example 3 also includes the subject matter according to any one of examples 1-2, above.

The micro air pump unit generates at least five hundred Pascals of pressure. The preceding subject matter of this paragraph characterizes example 4 of the present disclosure, wherein example 4 also includes the subject matter according to any one of examples 1-3, above.

The micro air pump unit consumes less than two Watts of power when operating. The preceding subject matter of this paragraph characterizes example 5 of the present disclosure, wherein example 5 also includes the subject matter according to any one of examples 1-4, above.

The micro air pump unit produces airflow of between one liter per minute and two liters per minute. The preceding subject matter of this paragraph characterizes example 6 of the present disclosure, wherein example 6 also includes the subject matter according to any one of examples 1-5, above.

The apparatus further includes a collar assembly, wherein the controller assembly is coupled to the collar assembly and the collar assembly is coupled to the reservoir and to the tube. The preceding subject matter of this paragraph characterizes example 7 of the present disclosure, wherein example 7 also includes the subject matter according to any one of examples 1-6, above.

The collar assembly includes an exhaust passageway fluidly connecting the internal cavity of the reservoir with an exhaust opening on the controller assembly. The preceding subject matter of this paragraph characterizes example 8 of the present disclosure, wherein example 8 also includes the subject matter according to example 7, above.

The collar assembly includes a collar inlet port, a collar exhaust aperture, and a collar exhaust channel. The preceding subject matter of this paragraph characterizes example 9 of the present disclosure, wherein example 9 also includes the subject matter according to any one of examples 7-8, above.

The collar exhaust aperture is located on a first side of the collar inlet port, and the collar exhaust channel is a passageway extending from the first side of the collar inlet port and around the collar inlet port to a second side of the collar inlet port and out a side of the collar assembly. The preceding subject matter of this paragraph characterizes example 10 of the present disclosure, wherein example 10 also includes the subject matter according to any one of examples 7-9, above.

The apparatus further includes a diffuser tip connected to the end of the tube below the oil level in the reservoir body, and the plurality of orifices are located on the diffuser tip. The preceding subject matter of this paragraph characterizes example 11 of the present disclosure, wherein example 11 also includes the subject matter according to any one of examples 1-10, above.

The plurality of orifices in the diffuser tip are recessed into the diffuser tip from an outer surface of the diffuser tip. The preceding subject matter of this paragraph characterizes example 12 of the present disclosure, wherein example 12 also includes the subject matter according to any one of examples 1-11, above.

The air inlet port includes an angled channel. The controller assembly and the base are electronically connected through a serial communication cable and wherein the controller assembly and the base are configured to permit bi-directional communication. The preceding subject matter of this paragraph characterizes example 13 of the present disclosure, wherein example 13 also includes the subject matter according to any one of examples 1-12, above.

The base includes a first port configured to electronically connect to the controller assembly and a second port configured to electronically connect to an external device. The preceding subject matter of this paragraph characterizes example 14 of the present disclosure, wherein example 14 also includes the subject matter according to any one of examples 1-13, above.

The second controller is configured to control the first controller, and wherein the second controller is configured to receive wireless communication from a remote computing device. The preceding subject matter of this paragraph characterizes example 15 of the present disclosure, wherein example 15 also includes the subject matter according to any one of examples 1-14, above.

The tube further includes a side aperture in a wall of the tube, wherein the side aperture is located at least one-half a height of the tube. The preceding subject matter of this paragraph characterizes example 16 of the present disclosure, wherein example 16 also includes the subject matter according to any one of examples 1-15, above.

Disclosed herein is an apparatus for diffusing essential oils into the air according to one or more examples of the present disclosure. The apparatus includes a reservoir configured to hold essential oils in an internal cavity, and a controller assembly removably coupled to the reservoir, the controller assembly including an air inlet port, a first controller, and a micro air pump unit. The apparatus further includes a base removably coupled to the controller assembly, the base including a second controller, wherein the second controller is connected to the first controller. The apparatus further includes a tube in fluid connection at a first end with the micro air pump unit and extending into the reservoir, the tube providing a path for pressurized air from the micro air pump unit into the reservoir through a plurality of orifices at a second end of the tube. The micro air pump unit generates at least five hundred pascals of pressure, and the micro air pump unit consumes less than one Watt of power when generating the at least five hundred pascals. The preceding subject matter of this paragraph characterizes example 17 of the present disclosure.

The micro air pump unit is a piezoelectric diaphragm micro pump. The preceding subject matter of this paragraph characterizes example 18 of the present disclosure, wherein example 18 also includes the subject matter according to example 17, above.

The apparatus further includes a collar assembly. The controller assembly is coupled to the collar assembly and the collar assembly is coupled to the reservoir and to the tube. The collar assembly includes an exhaust passageway fluidly connecting the internal cavity of the reservoir with an exhaust opening on the controller assembly. The collar assembly includes a collar inlet port, a collar exhaust aperture, and a collar exhaust channel. The collar exhaust aperture is located on a first side of the collar inlet port. The collar exhaust channel is a passageway extending from the first side of the collar inlet port and around the collar inlet port to a second side of the collar inlet port and out a side of the collar assembly. The preceding subject matter of this paragraph characterizes example 19 of the present disclosure, wherein example 19 also includes the subject matter according to any one of examples 17-18, above.

Disclosed herein is a method of infusing air with essential oils according to one or more examples of the present disclosure. The method includes providing an essential oils reservoir, coupling a controller assembly to the reservoir, the controller assembly including a micro air pump unit, and a first controller. The method further includes coupling a base to the reservoir, the base including a second controller. The method further includes controlling operation of the first controller through the second controller to operate the micro air pump unit and expel air through the controller assembly into a tube and into essential oils located in the reservoir. The preceding subject matter of this paragraph characterizes example 20 of the present disclosure.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which:

FIG. 3 is a side view of a straw, base, and diffuser tip of a diffusing apparatus, according to one or more embodiments of the present disclosure;

FIG. 4 is an exploded view of a controller assembly and bottle interface, including a foaming reduction device for a diffusing apparatus, according to one or more embodiments of the present disclosure;

FIG. 25 is a side view of a reservoir, according to one or more embodiments of the present disclosure;

FIG. 26 is a side view of the reservoir, according to one or more embodiments of the present disclosure.

DETAILED DESCRIPTION

Figure 1:
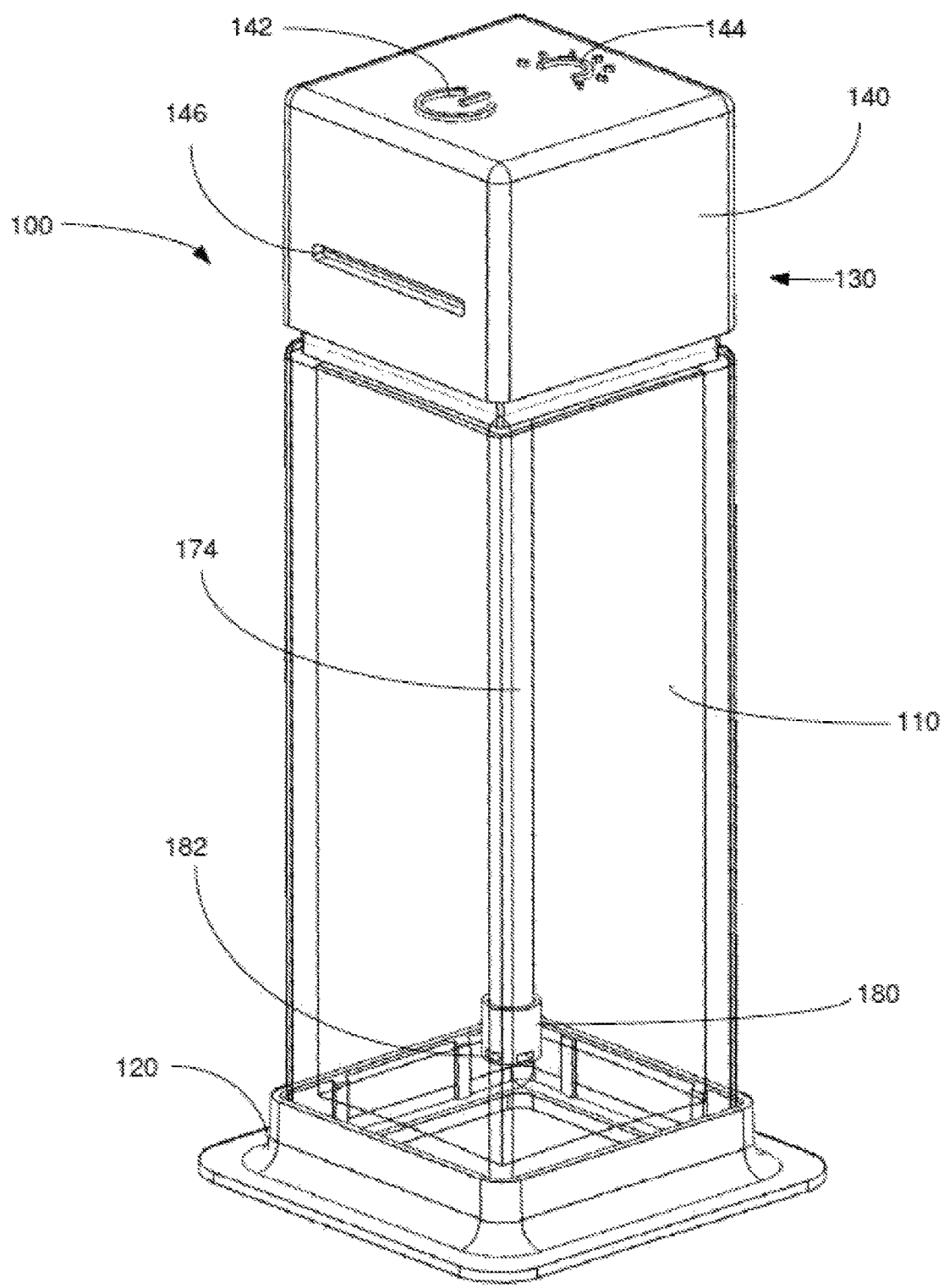
FIG. 1 is a perspective view of a diffusing apparatus, according to one or more embodiments of the present disclosure.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

The following description supplies specific details in order to provide a thorough understanding. Nevertheless, the skilled artisan would understand that the apparatus and associated methods of using the apparatus can be implemented and used without employing these specific details. Indeed, the apparatus and associated methods can be placed into practice by modifying the illustrated apparatus and associated methods and can be used in conjunction with any other apparatus and techniques conventionally used in the industry.

Exemplary essential oils diffusers may utilize an optimized and unique design to effectively diffuse many different types of essential oils with or without any added water into a personal space or room for many hours of enjoyment. Essential oils diffusers disclosed herein may use a piezoelectric micro air pump or other suitable micro air pump to diffuse air within a well or reservoir of essential oils. Diffusing air in essential oils causes an efficient saturation of oil in the air within air bubbles. Indeed, bubbles provide efficient and dynamic oil diffusion into the air by providing extended exposure of the air to a maximum surface area compared to volume of air, thereby infusing the air with essential oils for dispersal in a room or other personal environment. Furthermore, diffuser tips also provide a calming sound of bubbling water as compared to the high frequency whine of traditional air fans and blowers. Suitable micro air pumps may provide between 500 and 2700 Pa of pressure with a consumption of between 0.1 and 1 Watts and deliver about 1-2 L/min of airflow in a physical package of less than 25×25×10 millimeters. In some embodiments, the physical package is less than 20×20×2 millimeters.

Through experimentation, it was discovered that a head pressure of at least 500 Pa is required to create bubbles 1 inch under the surface of light viscosity essential oils. Heavier essential oils and deeper reservoirs, or course, require higher pressures to permit bubbling. It was also discovered that commercially available traditional fan and blower designs were incapable of delivering the required pressure for submerged bubbling air infusion to push air into essential oils or an essential oil solution to diffuse and expel the oils into the air, while keeping the oils away from the air pump, preventing the oils from shortening the life of the diffuser. As shown in the Figures, essential oils diffusers 100 that are suitable to generate effective, efficient submerged bubbling diffusion may include a controller assembly 130, a reservoir (bottle) 110, base 120, and a tube 174 and diffuser tip 180 that extend into the reservoir 110. Effective diffusers using the components illustrated may measure less than 155 mm tall including reservoir and less than 30×30 millimeters, with a controller/air pump assembly of less than 30 millimeters cubed to provide an efficient, effective micro diffuser.

Figure 2:
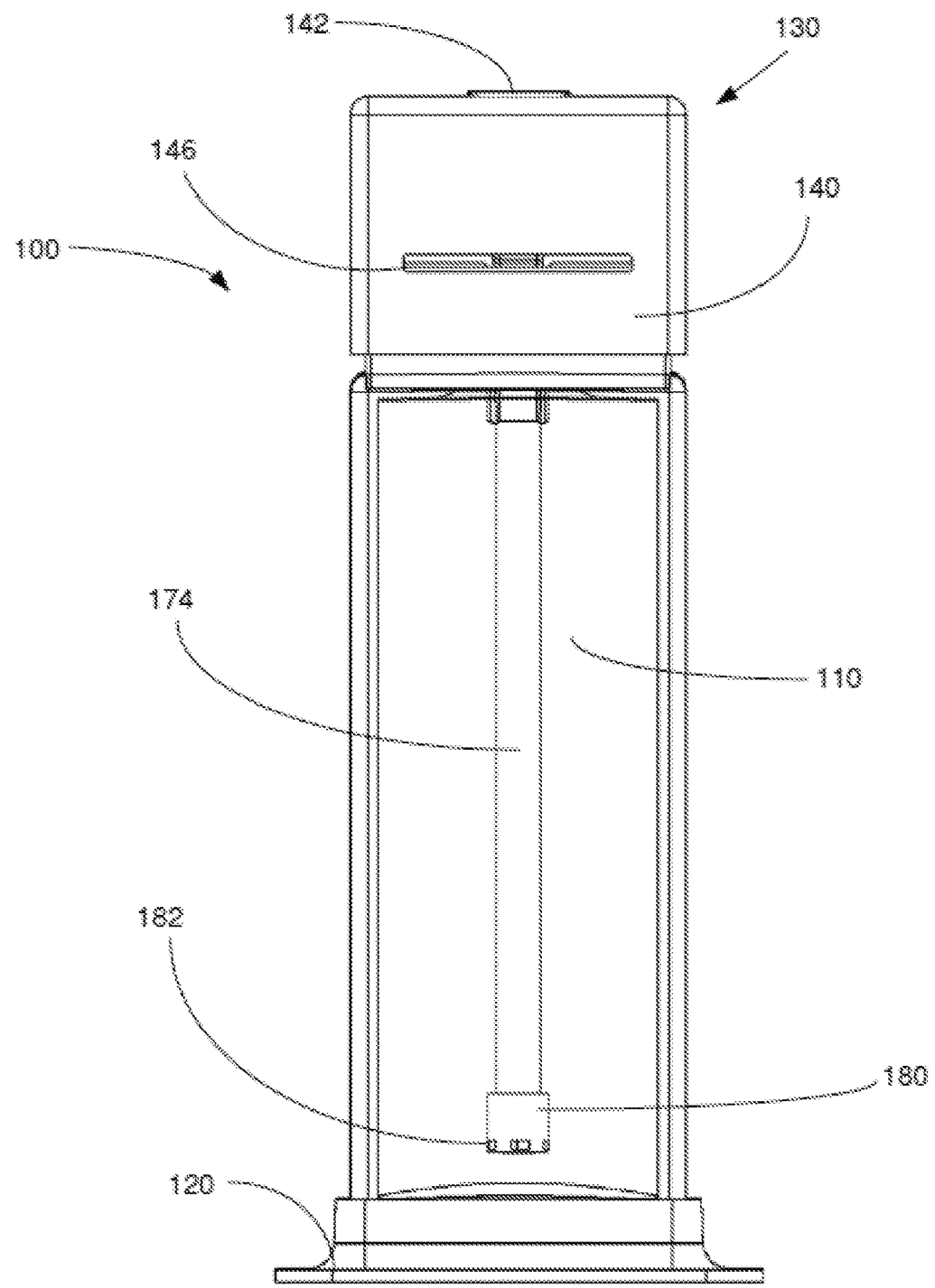
FIG. 2 is a front view of a diffusing apparatus, according to one or more embodiments of the present disclosure.

Turning first to FIGS. 1 and 2, diffusing apparatus 100 may include a controller assembly 130 with a protective cap 140 mounted on a reservoir 110. Reservoir 110 may be placed in base 120 to stabilize diffusing apparatus 100 to reduce the likelihood of spills, tip-overs, or unwanted vibrations. Protective cap 140 may house the controller assembly 130, which will be discussed in more detail below, oil infused air exhaust opening 146, and buttons 142 and 144 for operating diffusing apparatus 100. Controller assembly 130 may be removably secured to reservoir 110 using gaskets and may include tube 174 extending from the bottom of controller assembly 130 and to near the bottom of reservoir 110. At the end of tube 174, diffuser tip 180 may include a plurality of holes 182 to bubble air into essential oils within the reservoir. As shown in FIG. 3 a bubble disruptor 176 may be included on tube 174 to keep any oil bubbles from pushing liquid oil out through cap base 170 and exhaust opening 146 to prevent oil sputter or droplets from collecting around diffusing apparatus 100.

FIGS. 3 and 4 shown exploded views of the various components and will be used to explain the various components of the illustrated embodiments and the function of diffusing apparatus 100. Controller assembly 130 may include cap 140 covering the internal components and providing an aesthetic package for diffusing apparatus 100. Touch sensitive capacitive electronic switches or sensor pads 132 and 134 may be operated by touching buttons 142 and 144 of cap 140. Button 142 may be used to select air flow rates and button 144 may be used to select lighting of one or more LEDs 133 to provide an attractive aesthetic to diffusing apparatus 100. The internal components may include a printed circuit board controller 131 with electronic components to provide light and control micro air pump 150. Controller 131 may include wireless capabilities, and may be programmable using a USB or other suitable interface. Similarly, a USB cord may be used to power diffusing apparatus 100 because of the low power requirement of micro air pump 150 and controller assembly 130.

Micro air pump 150 may be a piezo air pump meeting the specifications discussed above. Spacers 136 and 138 may be provided to separate the fresh air supply into air pump 150 and the output air from air pump 150. Pump base 154 may be secured to controller 131 with fasteners 135 to secure the controller/air pump assembly 130 together. Gasket 156 may be used to create an air-tight interface between the air output of air pump 150 and cap base 170.

Cap base 170 may be formed to secure controller assembly 130 to reservoir 110, and to direct air into tube and infused air out through opening 172. Cap base 170 may be securely placed on reservoir 110 with the aid of gasket 112 on the neck 114 of reservoir 110. Cap base 170 may be part of controller assembly 130 or may be used as a cap for reservoir 110. In such embodiments, switching reservoirs is very simply accomplished by pulling controller assembly 130 off of base cap 170 and placing in on a different reservoir with another base cap installed.

Figure 5:
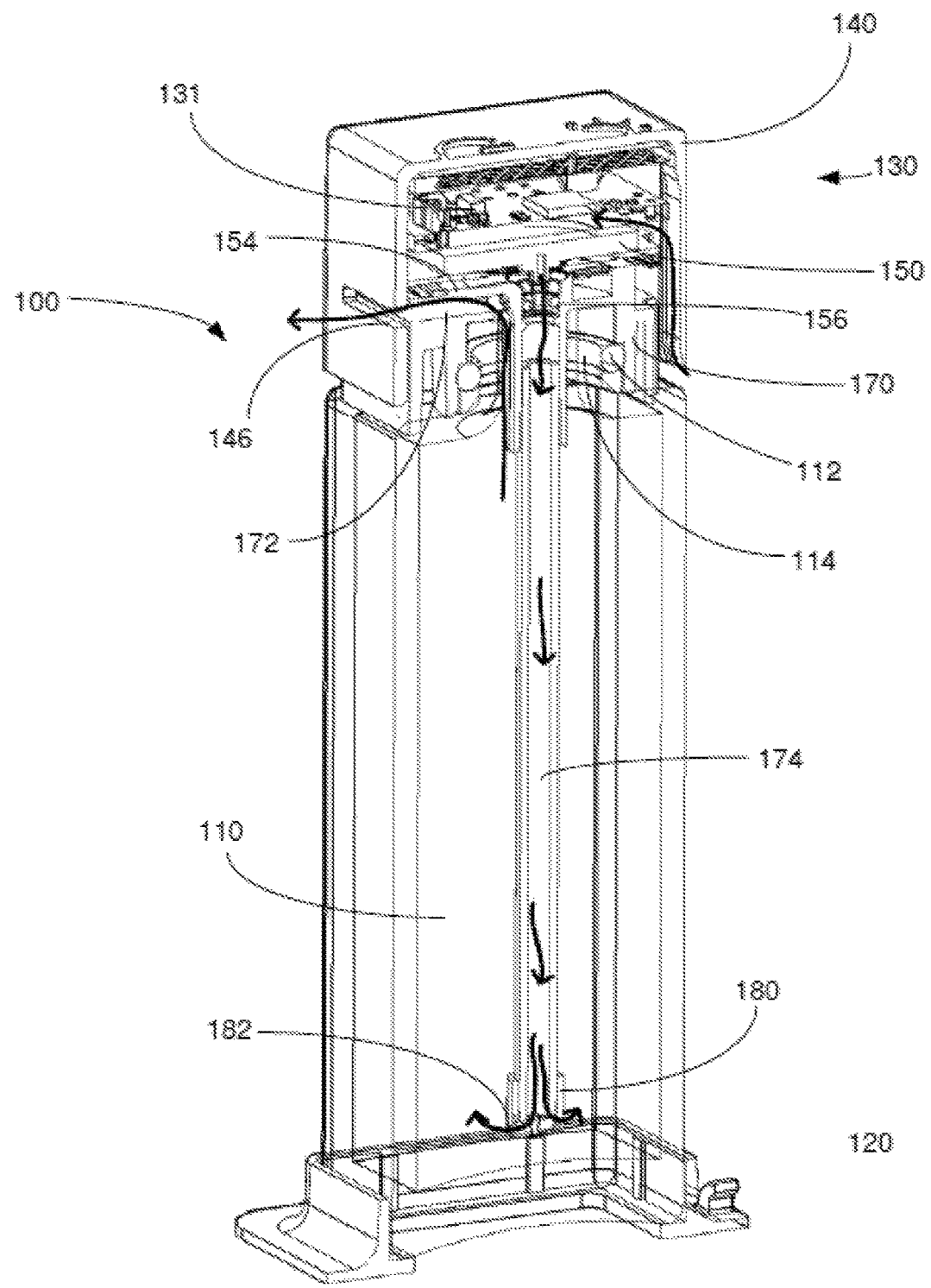
FIG. 5 is a cross-sectional view of a diffusing apparatus, according to one or more embodiments of the present disclosure.
Figure 6:
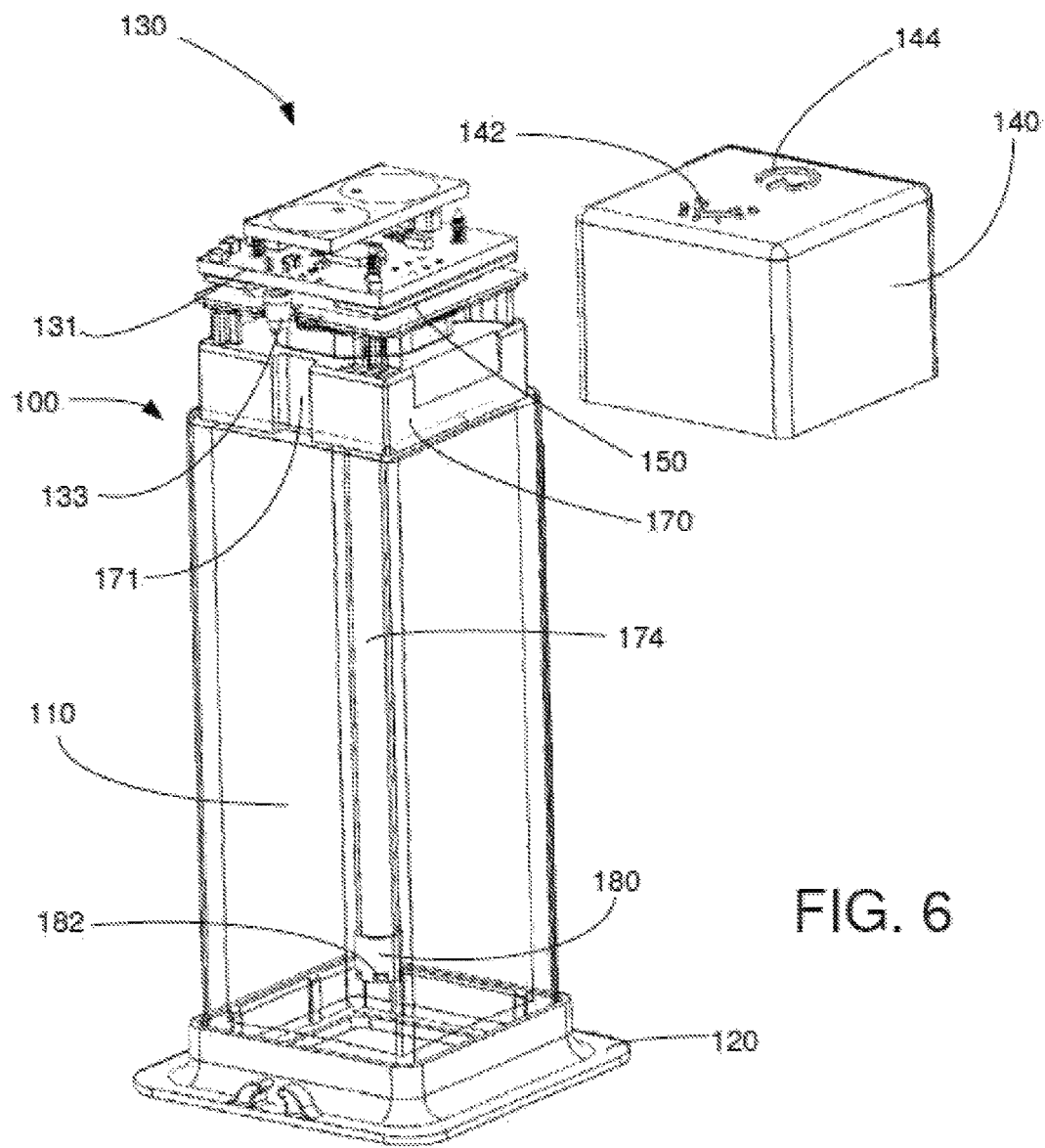
FIG. 6 is a perspective view of a diffusing apparatus while partially disassembled, according to one or more embodiments of the present disclosure.

Turning now to FIGS. 5 and 6, the path of air through diffusing apparatus 100 can be easily seen. Fresh air enters under the rear of protective cap 140, along channel 171 in cap base 170, into air pump 150, and is then pumped down through cap base 170 and into tube 174 into reservoir 100. At the bottom of tube 174, diffuser tip 180 includes a plurality of openings 182 to create bubbles when air is pumped into essential oils in reservoir 110. The bubbles may then rise through the essential oils in reservoir 110, ideally bursting at the surface. The oil infused air can then exit though cap base 170 opening 172 and out through exhaust opening 146.

Diffuser tip 180 may be designed with different sizes and configurations of openings 182 depending on the size and frequency of bubbles desired, as well as depending on the viscosity of the essential oil to be diffused. For example, smaller openings 182 may provide small bubbles, which may provide maximum efficiency in diffusing oils into the air within the bubbles as the available surface area per volume of air is maximized. In some embodiments, the sound of the bubbles can be tuned to generate an aesthetically pleasing sound based on the size and frequency of the bubbles based, again, on the number and sizes of openings 182 and the viscosity of the oil. For example, diffuser tip 180 may include 6 openings 182, or 12 openings 182.

Reservoir 110 may comprise of an easily removable glass or molded polymer body that is optimized dimensionally with the diffuser for greatest effect by allowing the most oils to be diffused in an effective manner before requiring a refill. In some embodiments, the reservoir may be bottles that are provided with essential oils by distributors and manufacturers. It may also be fitted with specially designed cap base 170 as discussed above. Referring to FIG. 26, the dotted lines signify internal surfaces. Such internal surfaces are still visible when the reservoir 110 is made of glass or similar transparent material.

In some embodiments, exhaust ports or emitters can be a small series of holes or other physical opening in the cap 140 and cap base 170 or at a body at the top of the reservoir that allows the pressurized air and volatiles to escape into the space or room to be diffused. These holes or opening can be closed or regulated via a valve or mechanism, or by simply tightening the reservoir to the cap for long-term storage during periods of non-use. This design may have the advantage of very good diffusion rates (consumption of essential oil) that can create a noticeable and potent aroma from a very small package and low relative energy consumption. This may be a desirable feature for essential oil companies as it promotes consumption of the products.

Exemplary essential oils diffusers as described herein provide superior diffusion compared to a simple fan that can only evaporate or blow air onto the surface of the essential oil or saturated pad. In contrast, the micro air pump injects pressurized air into the bottom of the reservoir, delivering a long, uninterrupted performance with great aromatic effect. Interestingly, a separate external fan can be utilized that blows fresh air into the diffused air stream after it exits the diffuser to further distribute the aroma if desired.

In some embodiments, the micro air pump may be located within a very short distance of the point of diffusion, or air discharge. This would enable the internal warmth of the device due to its operation to be quickly carried with the pressurized air to the diffusion point, further enhancing diffusion efficiency. The illustrated designs and others may permit incoming air flow to flow past and cool all electronic components to increase the warmth of the input pressurized air introduced into the essential oil reservoir. However, if the design requires, it can be located further away for more design freedom.

In some embodiments, the micro air pump can be modulated to create different flow rates by varying the amplitude of the sinusoidal drive signal for adjustable flow. Or it can be controlled in an adjustable interval On/Off mode for periodic diffusion. Alternatively, the flow rate can be controlled by reducing the diffuser emitter (exit) opening by adjusting a mechanism or tightening the reservoir bottle. Because of its small size, the micro air pump can be located unobtrusively and almost invisibly in many areas of the diffuser. One optional micro air pump may be only a few millimeters thick and have a footprint of only 20 mm×20 mm square. This permits the diffuser to achieve many novel, different, and even minimal designs that will create a differentiated look. Additionally, the LED can be modulated to create a different mood or lighting effect.

In other embodiments, the controller assembly 130 may also include wireless communication capability to allow for control from a wireless device such as a cell phone or other computer. Similarly, the control functionality may be modified in numerous ways with air flow and lighting modifications as desired.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, examples are meant to be illustrative only and should not be construed to be limiting in any manner.

Figure 7:
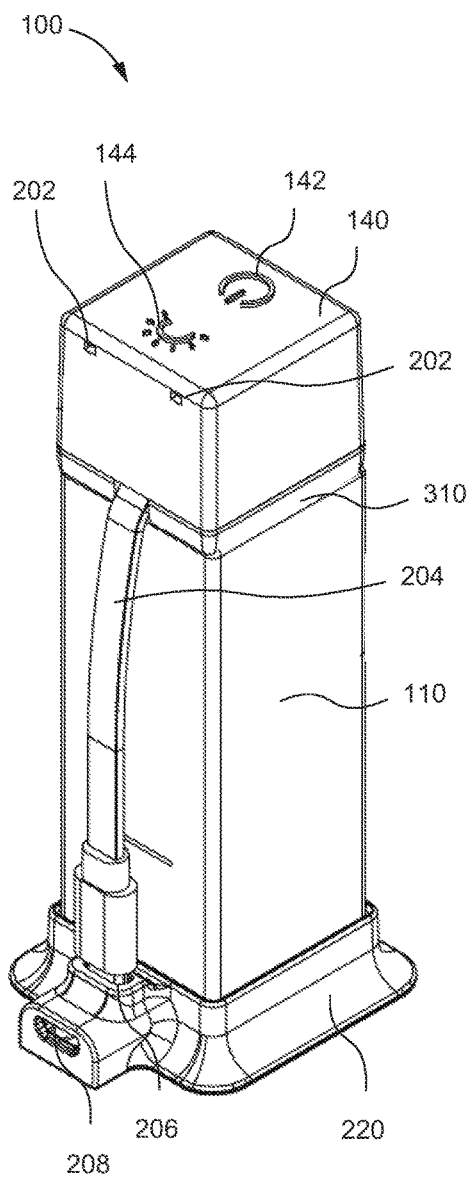
FIG. 7 is a perspective view of a diffusing apparatus, according to one or more embodiments of the present disclosure.

Referring to FIG. 7, a perspective view of a diffusing apparatus 100 is shown. The diffusing apparatus 100 includes a base 220, a reservoir 110, a collar assembly 310, and a controller assembly 130. Although the diffusing apparatus 100 is shown and described with certain components and functionality, other embodiments of the diffusing apparatus 100 may include fewer or more components to implement less or more functionality.

The diffusing apparatus 100 described in conjunction with FIG. 7 may include some or all of the features described in conjunction with FIGS. 1-6 and are not repeated for the sake of brevity.

The diffusing apparatus 100 includes a base 220. The base 220 is a support structure configured to support the reservoir 110. The base 220 includes a printed circuit board base controller 224 configured to interconnect and communicate with the printed circuit board controller 131. The base 220 may include various components configured to facilitate the communication between the printed circuit board base controller 224 and the printed circuit board controller 131.

Communication between the printed circuit board base controller 224 and the printed circuit board controller 131 is implemented through a wired connection. However, the communication between the printed circuit board base controller 224 and the printed circuit board controller 131 may be, in other embodiments, facilitated by various wireless communication processes including Wi-Fi or Bluetooth etc.

The communication between the printed circuit board base controller 224 and the printed circuit board controller 131 may allow for the printed circuit board base controller 224 to control the printed circuit board controller 131 or for the printed circuit board controller 131 to control the printed circuit board base controller 224. Communication and control is configured to be bi-directional. In addition, the bi-directional communication and control permits a user to swap out a base 220 for another base 220 (see for example FIG. 11) that includes different components and features.

The interchangeability of a base 220 allows for a user to upgrade or replace a base 220 without the need to replace the remaining components of the diffusing apparatus. The controller assembly 130 may be configured to detect the type of base 220 interconnected to the controller assembly 130. Such detection may be done in a variety of manners including by detecting a signal. In an embodiment, the use of a pull-up resistor or pull-down resistor may indicate the type of base 220. For example, a signal from a pull-down resistor may indicate a base 220 is an active base, which may indicate bi-directional control capabilities, and a pull-up resistor may indicate a base 220 a passive base, which may indicate that the controller assembly 130 will control the base 220. The base 220 can be swapped out while allowing the controller assembly 130 to still operate. Various peripheral devices can be envisioned to connect and interface with the controller assembly 130, allowing for upgradeable components.

The base 220 is enabled with Bluetooth, Wi-Fi, or other similar wireless communication technology. The wireless communication technology is configured to allow a user to operate and control the base 220 through another computing device (not shown) including a mobile phone, tablet, laptop, computer, etc. In an example, the base 220 may be controlled through an application downloadable to a user's phone or computing device. The remote connection allows for a user to operate the diffusing apparatus 100 including the base 220 and the controller assembly 130 without the need of touching diffusing apparatus 100. A user may engage the diffusing apparatus 100 prior to returning to the user's home or office such that the diffusing apparatus 100 can have already diffused essential oils into a room upon arrival of the user.

The base 220 includes ports 206 and 208. External port 208 allows for the wired connection of the base 220 to an external device or an external power source. In an example, the base 220 may be connected through external port 208 to an electrical outlet via a micro USB cable. The power delivered from the electrical outlet may power the base 220 and the controller assembly 130. In another example, the base 220 may be connected through external port 208 to a computing device which may provide power and/or directions for controlling the base 220.

Although depicted as a micro USB port, the external port 208 may allow for the wired connection of the base through other communication interfaces including other serial communication interfaces. In an example, the communication interfaces may use full-duplex serial communication. In another example, the communication interfaces may use half-duplex serial communication. In some embodiments, the communication interfaces may include a full-duplex serial interface with power port. In some embodiments, the base 220 and/or controller assembly 130 includes a universal asynchronous receiver-transmitter (UART). A universal asynchronous receiver-transmitter is a computer hardware device for asynchronous serial communication in which the data format and transmission speeds are configurable. The universal asynchronous receiver-transmitter may be part of the printed circuit board base controller 224, the printed circuit board controller 131, or both. Other hardware components similar to the universal asynchronous receiver-transmitter are also contemplated herein.

The base 220 also includes an internal port 206. Internal port 206 allows for the wired connection of the base 220 to the controller assembly 130. Referring to FIG. 7, the base 220 is wired to the controller assembly 130 through a USB cable 204. The USB cable 204 provides bi-directional serial communication between the controller assembly 130 and the base 220. While a USB cable 204 is depicted, other types of serial communication cables may be utilized.

Figure 9:
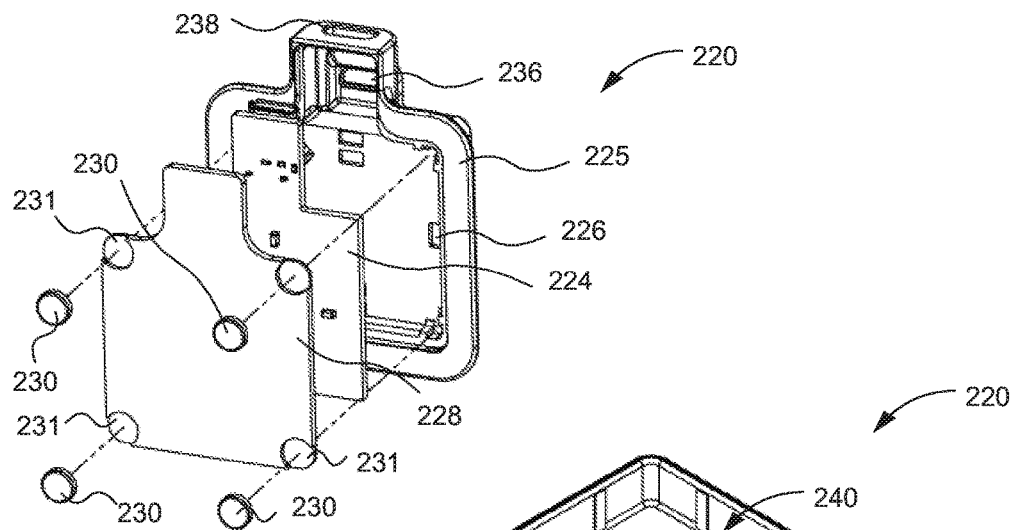
FIG. 9 is an exploded perspective view of a base, according to one or more embodiments of the present disclosure.
Figure 10:
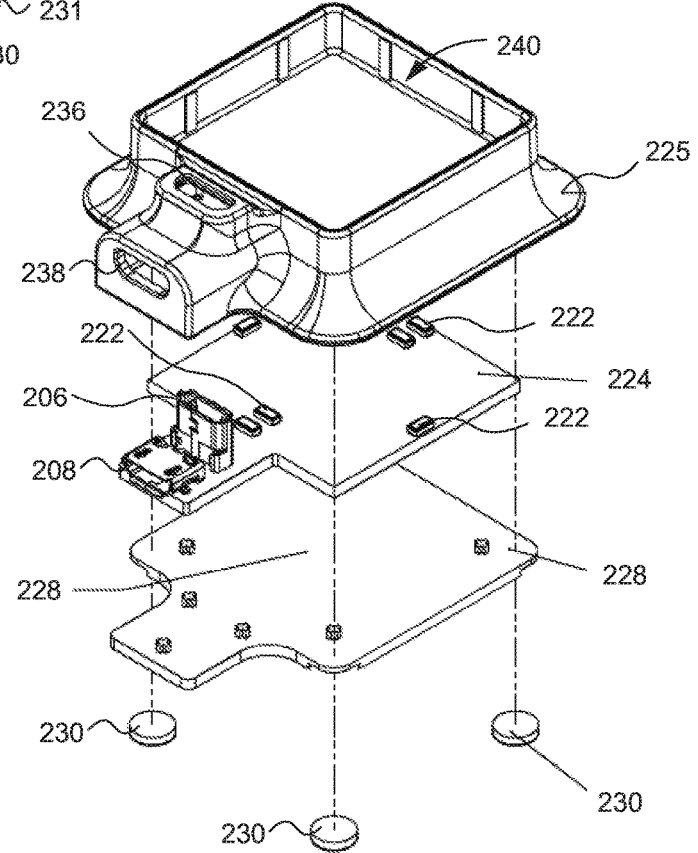
FIG. 10 is an exploded perspective view of the base, according to one or more embodiments of the present disclosure.

Referring to FIGS. 9 and 10, exploded views of a base 220 are depicted according to some embodiments of the invention. The base 220 includes an exterior casing 225, a printed circuit board base controller 224, and a flooring 228. Although the base 220 is shown and described with certain components and functionality, other embodiments of the base 220 may include fewer or more components to implement less or more functionality.

The base 220 includes an exterior casing 225. The exterior casing 225 includes a reservoir receptacle 240. The reservoir receptacle 240 is a support basin which is configured to support and hold the reservoir 110 allowing the reservoir 110 to stand upright. On a bottom surface of the reservoir receptacle 240, the base 220 includes a plurality of apertures 226. The apertures 226 are located in various locations along the bottom surface of the reservoir receptacle 240. The apertures 226 allow access for LEDs 222 located on the printed circuit board base controller 224 to illuminate through the exterior casing 225 and up onto the reservoir 110.

In an embodiment, the base 220 includes dual LEDs 222. Positioning LEDs 222 in the base 220 allows for the up-lighting of the reservoir and the essential oils during operation of the diffusing apparatus. The LEDs 222 may be controlled and operated in various ways. In an example, the LEDs 222 are controlled through an application on a remote computing device. In an example, the LEDs 222 are controlled by the controller assembly 130. As described above, the controller assembly 130 may communicate and control the base through the bi-directional communication facilitated by the USB cable 204. Although described as light emitting diodes, the LEDs 222 may, in some embodiments, be alternative lighting apparatuses.

Control of the LEDs 222 may occur through button 144 on the cap 140. In addition, the LEDs 222 may be powered by the controller assembly 130. As an example, various lighting conditions may be contemplated and configured that allow for strobing, pulsing, flickering, dimming and other effects. In addition, the LEDs 222 may function independently to allow for further options for illuminating the reservoir 110.

The exterior casing 225 further includes port openings 236 and 238 through which the ports 206 and 208 fit. The internal port 206 fits into the port opening 236 and the external port 208 fits into the port opening 238.

The base 220 further includes a printed circuit board base controller 224. As described above, the printed circuit board base controller 224 may include hardware and other circuits, including a universal asynchronous receiver-transmitter among other components. The printed circuit board base controller 224 is configured to allow communication to external devices and communication to the controller assembly 130. The printed circuit board base controller 224 may include software, which is updateable, that operates the diffusing apparatus 100, allowing for continual updating of the diffusing apparatus 100 with additional features. The printed circuit board base controller 224 may be described, in some embodiments, as a microcontroller unit or MCU.

The base further includes a flooring 228. The flooring 228 interfaces with the exterior casing 225 to enclose the printed circuit board base controller 224. Assembled with or otherwise attached to the flooring are rubber feet 230. The flooring 228 along with the exterior casing 225 may cooperatively protect the printed circuit board base controller 224 from external damage.

Figure 11:
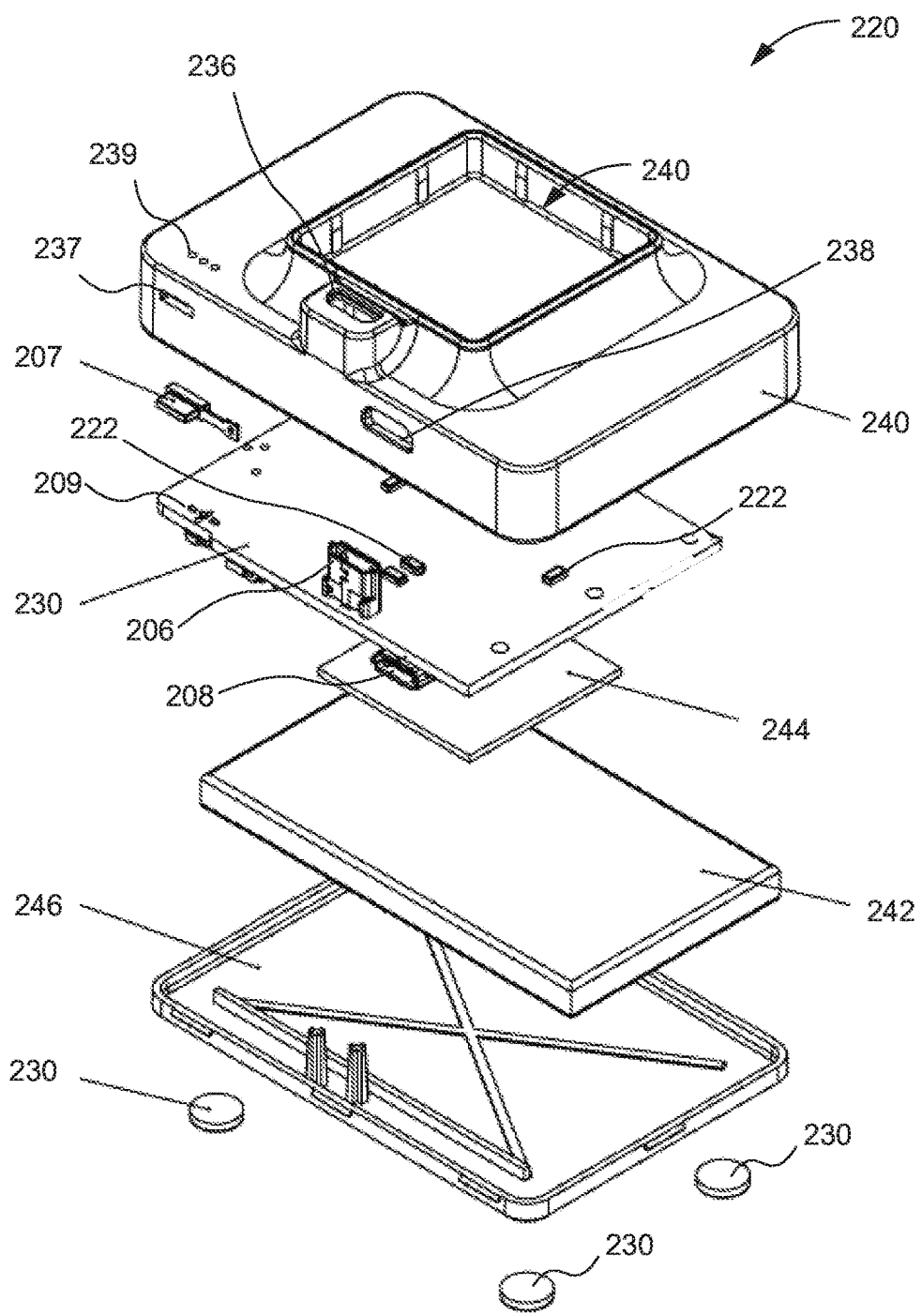
FIG. 11 is an exploded perspective view of a battery base, according to one or more embodiments of the present disclosure.

The base 220, in some embodiments, includes a power source configured to provide power to the diffusing apparatus 100. Referring to FIG. 11, an embodiment of a base 220 includes an independent power source. The base 220 includes an exterior casing 225, a printed circuit board base controller 224, an expandable foam 244, a power button 207, a battery 242, and a bottom cover 246. Although the base 220 is shown and described with certain components and functionality, other embodiments of the base 220 may include fewer or more components to implement less or more functionality.

In the illustrated embodiment, the base 220 includes a battery 242. The battery 242 may be any battery or device comprising an electrochemical cell that converts chemical energy into electrical energy including but not limited to a rechargeable battery, non-rechargeable battery, an alkaline battery, a lithium-ion battery, a lithium polymer battery, a nickel-cadmium battery, or any other type of battery. Additionally, the battery may be of any standard or special size including but not limited to D, C, AA, AAA, LR 44, 9-volt, etc.

As described above, the battery 242 may be a rechargeable battery, which is rechargeable through the power supplied to the external port 208. The battery 242 may include or be coupled with a battery protection circuit or other hardware or software that regulates the charging and discharging of the battery 242.

The battery 242 allows for the diffusing apparatus 100 to operate without a power cord and allows for the easy movement of the diffusing apparatus 100 to various locations that may not provide access to external power sources.

The battery 242 and the printed circuit board base controller 224 are enclosed by the exterior casing 225 and the bottom cover 246. Varieties of batteries expand and retract depending on the cycle of recharging/discharging. The base 220 may include an expandable foam 244 positioned between the battery 242 and the printed circuit board base controller 224 to protect the battery 242 and the printed circuit board base controller 224 from damage.

The base 220 may include a passive infrared sensor. A passive infrared sensor is an electronic sensor that measures infrared (IR) energy (heat) radiating from objects in its field of view and may be utilized in conjunction with a motion detector. The base 220 may be configured to "wake up" upon detecting motion within a room. The base 220 (or the controller assembly 130) may include software that is configured to enter the diffusing apparatus 100 into a sleep mode upon a period of time without motion detected in a room. Such a feature and components allow for the operation of the diffusing apparatus 100 when someone is going to sleep without the need of turning off the diffusing apparatus 100. The diffusing apparatus may operate for a period of time and enter sleep mode upon a passage of a predetermined time without motion detected by the passive infrared sensor. Although implemented with infrared technology, such motion detection may be accomplished by other means not described herein for the sake of brevity. Another sleep mode may be employed by software included in the base 220 (or the controller assembly 130) via a user command wherein the diffuser will operate for a preset period of time and then dynamically terminate power to the micro air pump at the end of the preset time period. The sleep mode command may be operated exclusively or simultaneously with other touch sensor commands.

Figure 8:
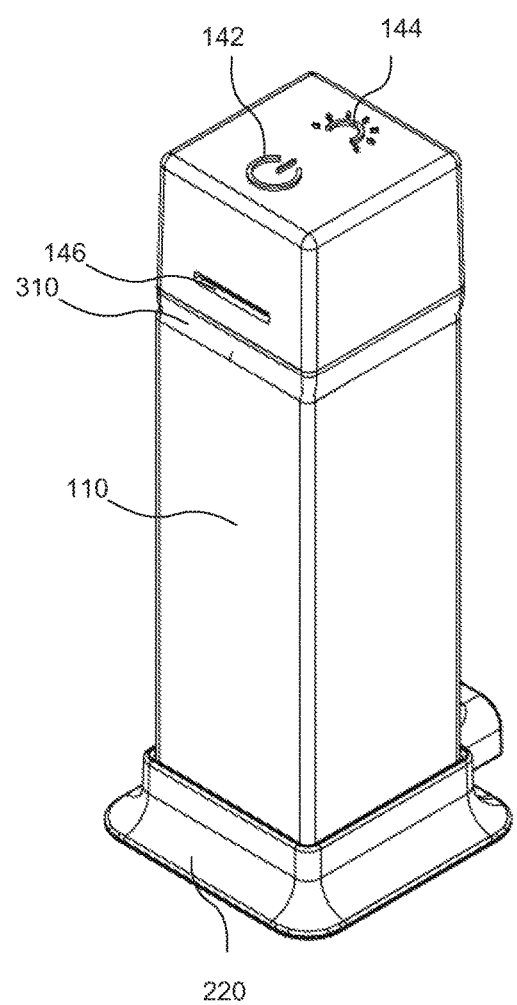
FIG. 8 is a perspective view of an opposite facing direction to the diffusing apparatus of FIG. 7, according to one or more embodiments of the present disclosure.

Referring back to FIGS. 7 and 8, the diffusing apparatus includes a reservoir 110. The reservoir 110 includes an internal cavity 163 which is configured to hold essential oils. The internal cavity 163 of the reservoir 110 may take different shapes and configurations. In an embodiment, the internal cavity 163 of the reservoir 110 includes contours at a bottom of the internal cavity 163. In an example, the internal cavity 163 includes a sloped and concave bottom surface which tapers to create a bowl at a bottom of the internal cavity 163 (see, FIG. 25). In some embodiments, the sloped and concave bottom surface may increase the surface area which increases bubble production and leads to increased aroma performance. In addition, the sloped and concave bottom surface may enhance lighting provided by LEDs 222.

Figure 12:
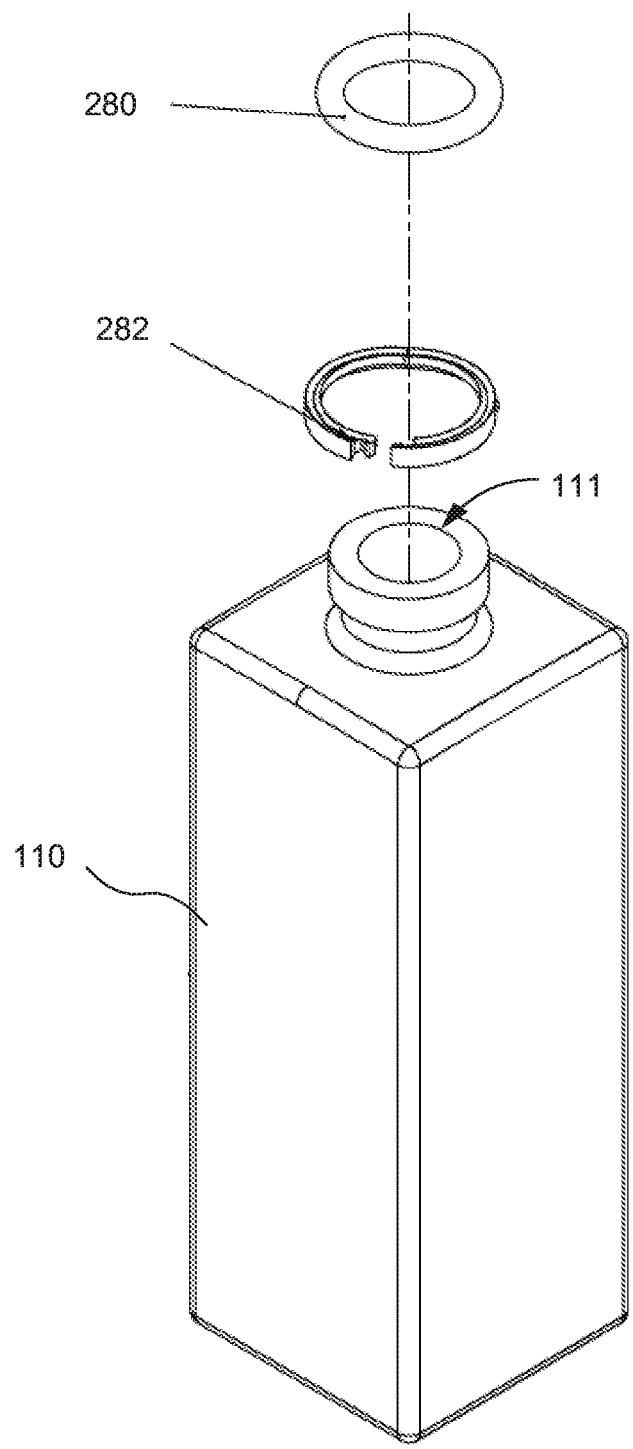
FIG. 12 is an exploded perspective view of a reservoir, according to one or more embodiments of the present disclosure.

The reservoir 110 includes a reservoir opening 111 (see, for example, FIG. 12). Essential oils may be poured into the reservoir 110 through reservoir opening 111. In addition, the air (or other fluid) input into the diffusing apparatus and the output also move through the reservoir opening 111 which is described in more detail herein.

The reservoir 110 interfaces with the controller assembly 130 and the collar assembly 310. To facilitate coupling of the various components, the diffusing apparatus 100 may include a snap ring 282 and an O-ring 280. The snap ring 282 and the O-ring 280 are configured to seal an outer surface of the reservoir opening 111 with the collar assembly 310 which will ensure that no input or output is lost through the interface between the reservoir 110 and the collar assembly 310. Some embodiments do not utilize the O-ring 280 and snap ring 282 but utilize the geometry of the reservoir opening 111 to couple and seal the collar assembly 310 to the reservoir 110. The snap ring 282 may be a machined or molded plastic part. The O-ring 280 may be an elastomer such as a fluoropolymer elastomer. Some embodiments may employ a square ring.

Referring to FIGS. 7-8 and 13-14, the diffusing apparatus 100 includes a controller assembly 130. The controller assembly of FIGS. 7-8 and 13-14 may include some or all of the features and components of FIGS. 1-6 or may include alternative features and components. Although the controller assembly 130 is shown and described with certain components and functionality, other embodiments of the controller assembly 130 may include fewer or more components to implement less or more functionality.

The cap 140 includes air inlet ports 202 and an exhaust opening 146. Air is drawn in through the air inlet ports 202 and proceeds through the diffusing apparatus 100 and is expelled through a tube 174 in the reservoir 110 by a micro air pump unit 290. The exhaust is propelled out the exhaust opening 146 similar to what is described in conjunction with FIGS. 1-6.

The air inlet ports 202 are located on an opposing side of the cap 140 to the exhaust opening 146. Such a configuration curbs any exhaust from the exhaust opening 146 from being drawn back into the diffusing apparatus 202 through the air inlet ports 202 to enable that the exhaust is disseminated into the room. In some embodiments, the air inlet ports 202 are square shaped ports. In some embodiments, the air inlet ports 202 are rectangular shaped ports. In some embodiments, the air inlet ports 202 are circle shaped ports. Other shapes and configurations are contemplated herein.

The air inlet ports 202, in some embodiments, each include an angled channel or passage, for example a ninety-degree elbow. The angled channel is configured to enable air to be drawn into the diffusing apparatus 100 but dampen sound waves generated by the controller assembly 130 and more specifically the micro air pump unit 290. The angled channel of the air inlet ports 202 allow for the quiet operation of the diffusing apparatus 100. In some embodiments, the angled channels are configured to reduce high frequency noise (6 kHz-22 kHz) produced by the micro air pump unit 290, while allowing full inlet air flow to the micro 290.

Figure 13:
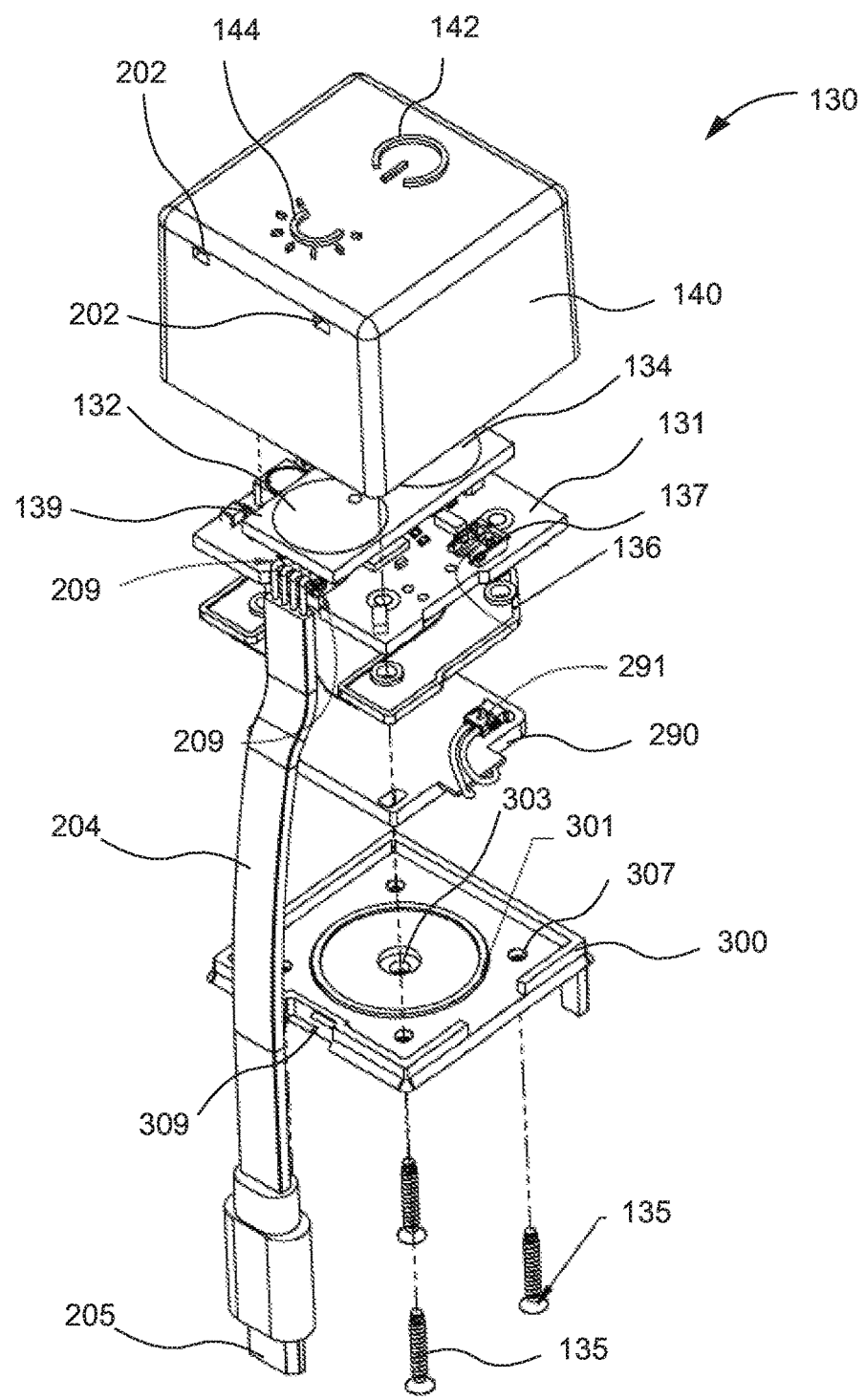
FIG. 13 is an exploded perspective view of a controller assembly, according to one or more embodiments of the present disclosure.
Figure 14:
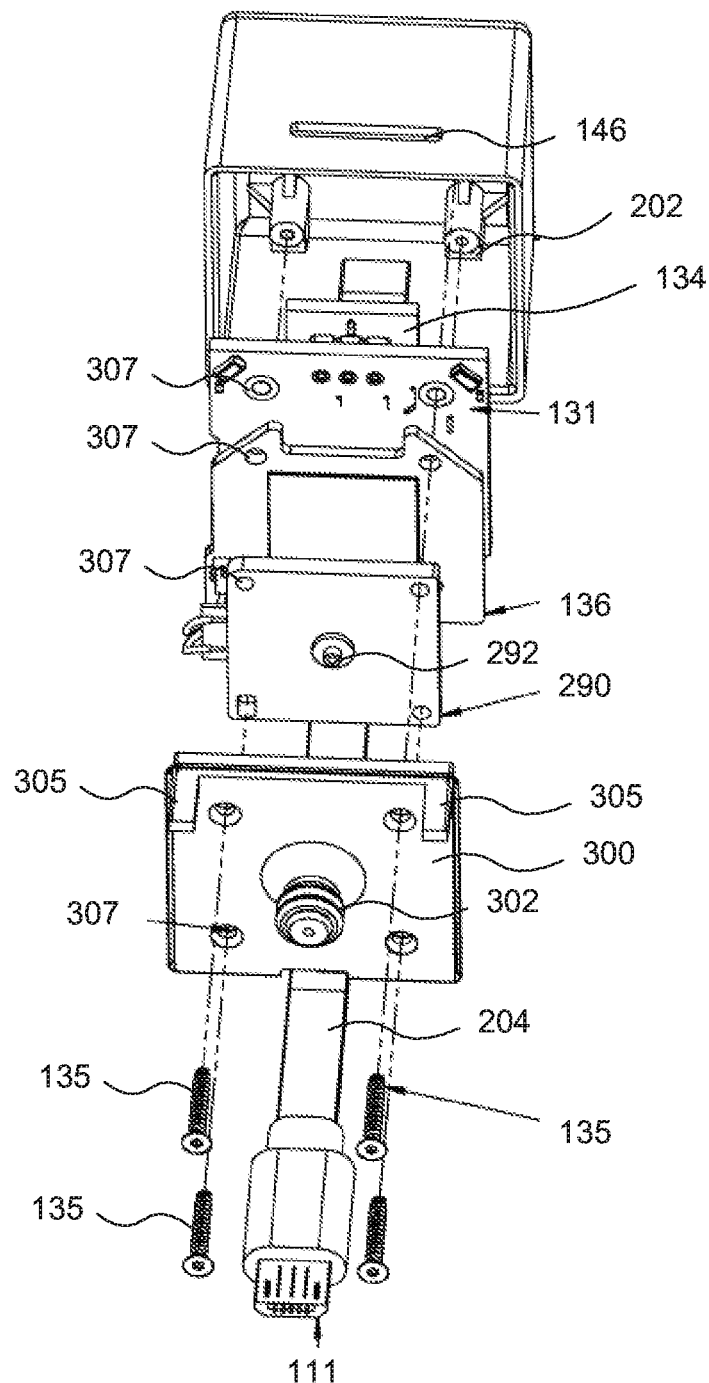
FIG. 14 is another exploded perspective view of the controller assembly of FIG. 13, according to one or more embodiments of the present disclosure.
Figure 15:
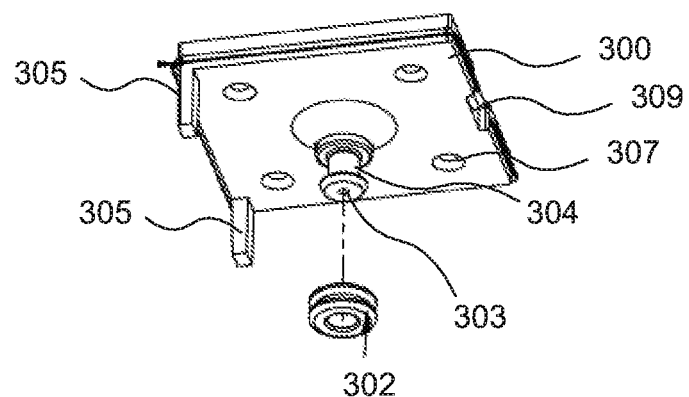
FIG. 15 is an exploded perspective view of an engine mount, according to one or more embodiments of the present disclosure.
Figure 16:
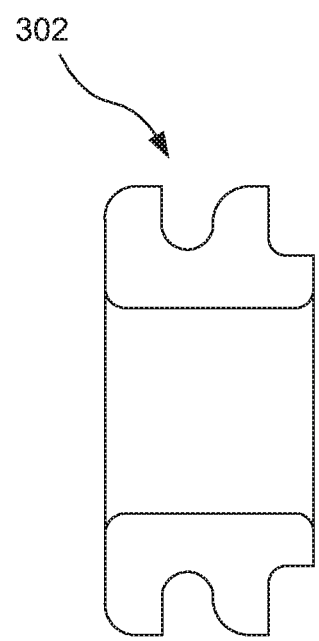
FIG. 16 is a cross-sectional side view of a wiper seal, according to one or more embodiments of the present disclosure.

Referring to FIGS. 13 and 14, the controller assembly 130 may include various components including a cap 140, a touch interface 139 including sensor pads 132 and 134, a printed circuit board controller 131, a spacer 136, a micro air pump unit 290, and an engine mount 300.

The micro air pump unit 290 draws air in from the air input ports 202 and pumps air out a nozzle 292. The air from the nozzle 292 is pumped down a central opening 303 of the engine mount 300. The micro air pump unit 290 functions similarly to what was described in conjunction with the micro air pump 150. The micro air pump unit 290 allows for operation of the diffusing apparatus 100 with low power consumption. In some embodiments, the micro air pump unit 290 is a piezoelectric diaphragm micro pump. In some embodiments, the micro air pump 290 may provide between 500 and 2700 Pa of pressure with a consumption of between 0.1 and 1 Watts and deliver about 1-2 L/min of airflow in a physical package of less than 25×25×10 millimeters. In some embodiments, the physical package is less than 20×20×2 millimeters. In addition, the pressure range may be dictated by the controller assembly 130 and may be dependent on the particular setting used. For example, a low setting may produce 500 Pa of pressure, a medium setting may produce 1200 Pa of pressure, and a high setting may produce up to 2700 Pa of pressure.

While the illustrated embodiments depict a single micro air pump 290, some embodiments may include a plurality of micro air pumps 290. In some implementations, the micro air pumps 290 are fluidly connected in series, which may increase the pressure ranges discussed above. In some implementations, the micro air pumps 290 are fluidly connected in parallel, which may increase the airflow range discussed above.

Each of the components of the controller assembly 130 may be fastened together through fasteners 135 and through apertures 307. The micro air pump unit 290 is coupled to the engine mount 300. The engine mount 300 is configured to couple to the collar assembly 310 (see, for example, FIGS. 17 and 18).

The engine mount 300 includes a central opening 303, a raised rim 301 and locating knobs 305. The central opening 303 extends from the top of the engine mount 300 and down through a central protrusion 304, which central protrusion 304 extends out the bottom of the engine mount 300. As described above, the central opening 303 funnels the air expelled through the nozzle 292 down the diffusing apparatus 100.

The central protrusion 304 is configured to align and couple with the collar assembly 310. More specifically, the central protrusion 304 is inserted into a collar inlet conduit 374 (see, for example, FIG. 18). Positioned on the central protrusion 304, the controller assembly 130 may include a wiper seal 302. The wiper seal 302, in the illustrated embodiment, is a double wiper seal with dual protruding sealing surfaces which are configured to couple to the collar inlet conduit 374 of the collar assembly 310.

The engine mount 300 further includes a raised rim 301 on which the micro air pump unit 290 rests and which forms a seal to ensure that the airflow expelled from the nozzle 292 is directed down the central opening 303.

The engine mount 300 further includes locating knobs 305 which are protrusions extending down at a periphery of the engine mount 300. The locating knobs 305 are configured to align with the collar assembly 310, and more specifically, with locating notches 315. The locating knobs 305 and the locating notches 315 cooperatively ensure that a collar exhaust port 312 aligns with the exhaust opening 146 of the cap 140.

The engine mount 300 further may include sealing edges located around a peripheral edge of the engine mount 300 to ensure that the engine mount 300 couples to the cap 140 and forms a seal to prevent fluid or other contaminants from entering into the controller assembly 130 through the bottom of the controller assembly 130. Further, the coupling between the engine mount 300 and the cap 140 prevents saturated output air from recirculating inside the controller assembly 130. In some embodiments, the sealing edges include a movable sealing flange molded into the engine mount.

The engine mount 300 further may include a cable slot 309 which permits USB cable 204 to pass between the engine mount and the cap 140 such that the USB cable 204 connects to the printed circuit board controller 131. The slot contains a protrusion to pinch the cable, holding it in place after assembly. As depicted in FIG. 13, the USB cable includes a lower connector 205 and an upper connector 209. The upper connector 209 is coupled to the printed circuit board controller 131. The coupling may be permanent. The lower connector 205 may connect to the base 220 as previously described herein.

The micro air pump unit 290 is connected to the printed circuit board controller 131 through a micro connector 291. The micro connector 291 couples to the printed circuit board controller 131 through controller connector 137. Through the electronic connection between the micro connector 291 and the controller connector 137, the printed circuit board controller 131 may control and operate the micro air pump unit 290.

Figure 17:
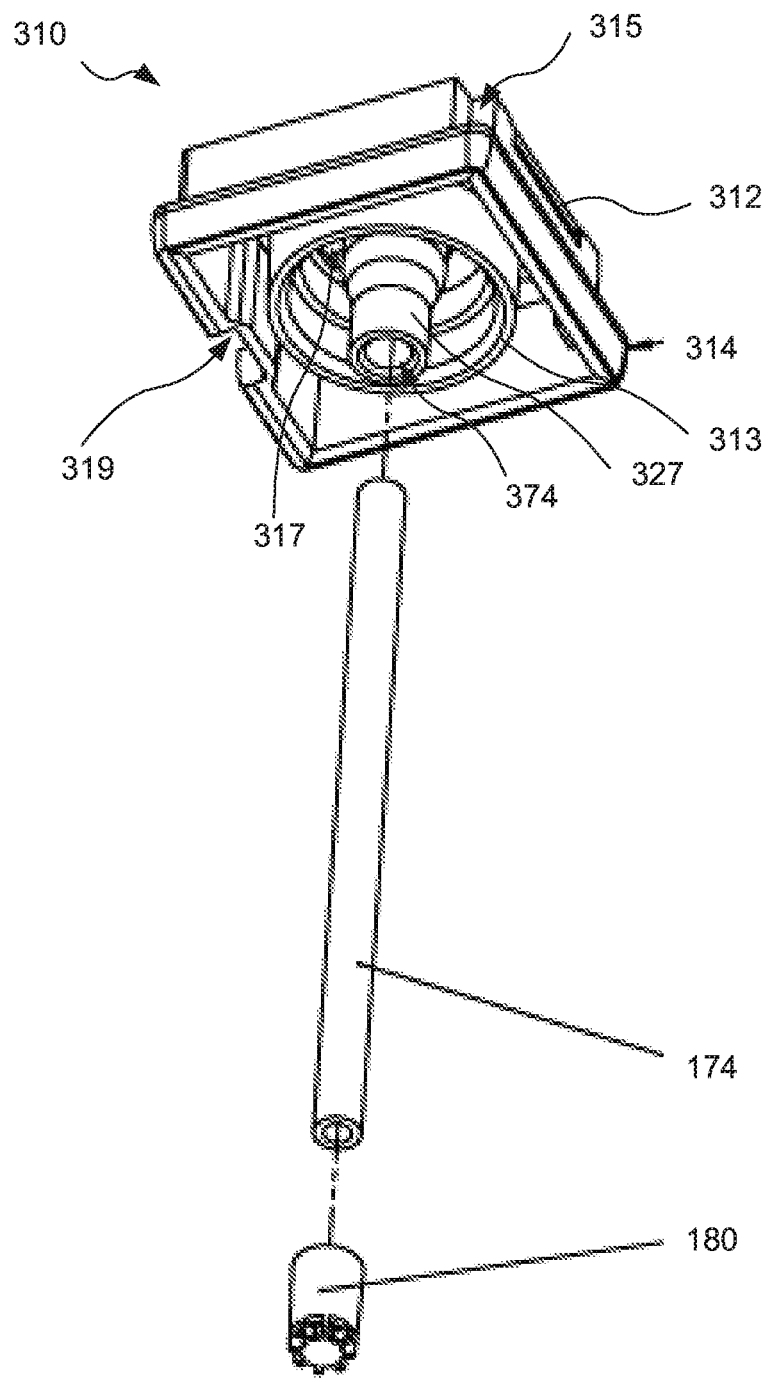
FIG. 17 is an exploded perspective view of a collar assembly, a tube, and a diffuser tip, according to one or more embodiments of the present disclosure.
Figures 18, 19:
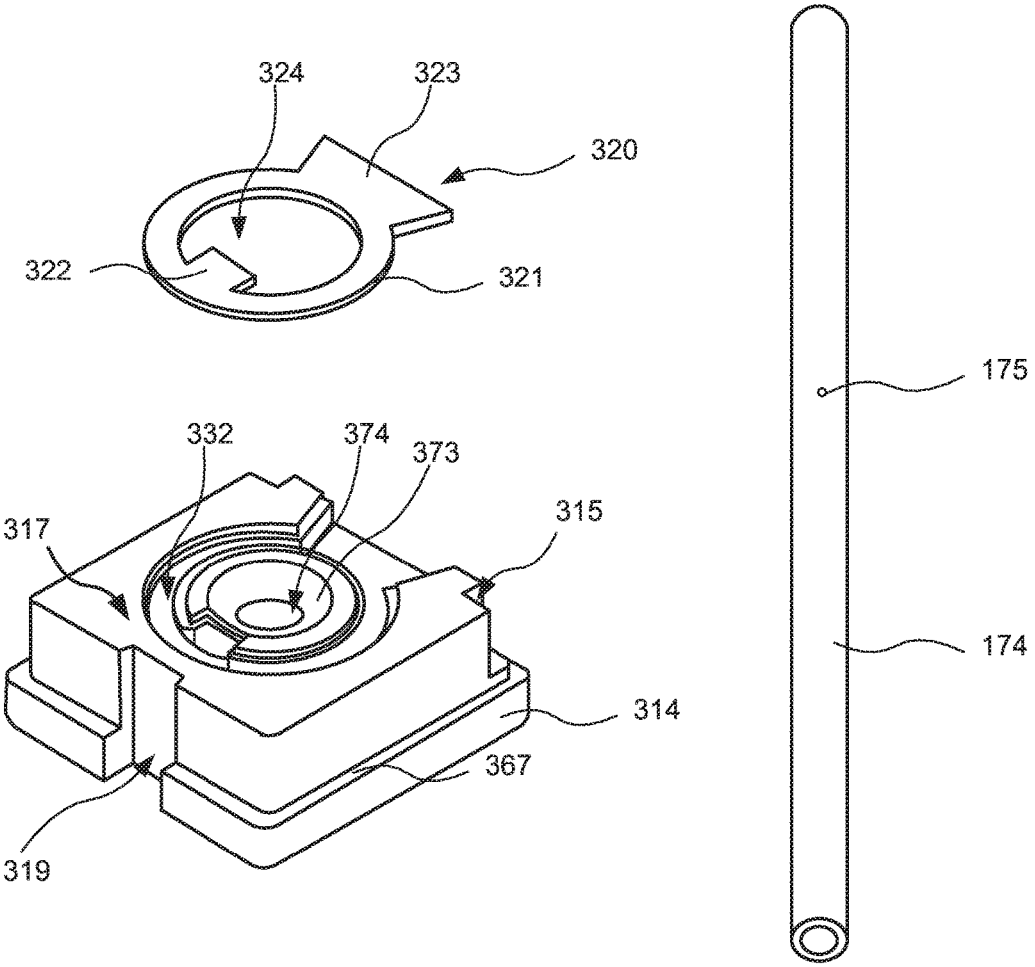
FIG. 18 is an exploded perspective view of a collar assembly, according to one or more embodiments of the present disclosure.
FIG. 19 is a perspective view of a tube, according to one or more embodiments of the present disclosure.
Figure 20:
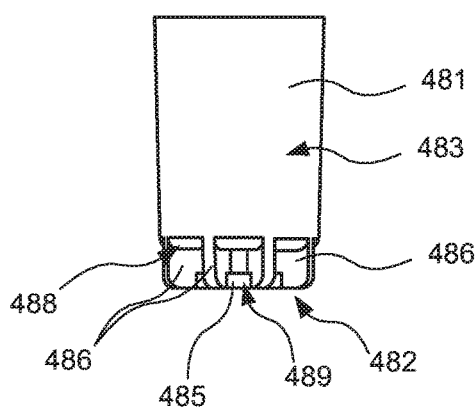
FIG. 20 is a side view of a diffuser tip, according to one or more embodiments of the present disclosure.
Figure 21:
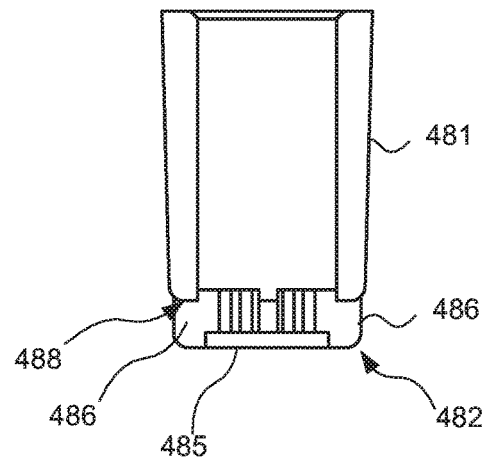
FIG. 21 is a side cross-sectional view of a diffuser tip, according to one or more embodiments of the present disclosure.
Figure 22:
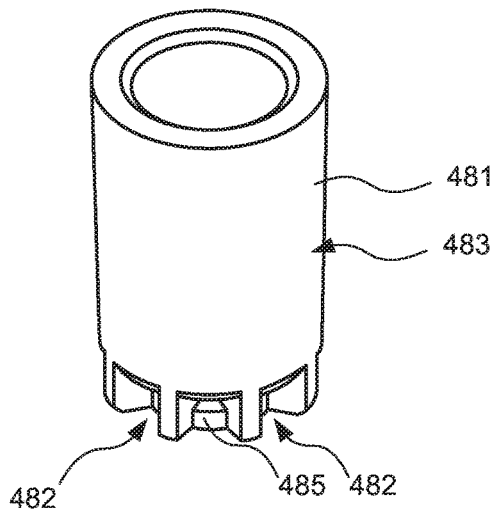
FIG. 22 is a perspective view of a diffuser tip, according to one or more embodiments of the present disclosure.
Figure 23:
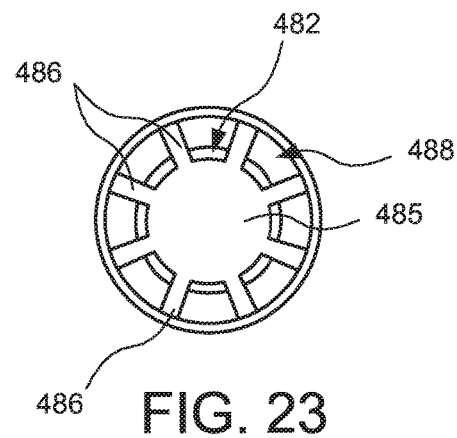
FIG. 23 is a bottom view of a diffuser tip, according to one or more embodiments of the present disclosure.
Figure 24:
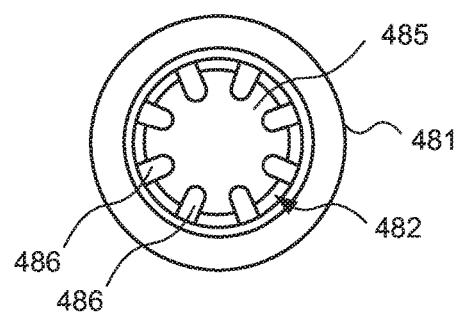
FIG. 24 is a top view of a diffuser tip, according to one or more embodiments of the present disclosure.

Referring now to FIGS. 17 and 18, the diffusing apparatus may include a collar assembly 310. The collar assembly 310 is configured, in some embodiments, to couple the controller assembly 130 to the reservoir 110 and to the tube 174.

The collar assembly 310 includes a collar 314 and a channel cap 320. Although the collar assembly 310 is shown and described with certain components and functionality, other embodiments of the collar assembly 310 may include fewer or more components to implement less or more functionality.

The collar 314 is a molded or machined part made of a solid material such as plastic. The collar 314 includes a collar inlet conduit 374 which is a centrally located conduit that channels the input air down into the tube 174. As discussed above, the central protrusion 304 is inserted into the upper opening of the collar inlet conduit 374 while the tube 174 is inserted into the lower opening of the collar inlet conduit 374. The collar inlet conduit includes a tapered surface 373 which is angled to allow for the controller assembly 130 to be inserted or removed at an angle. The tapered surface 373 allows for the controller assembly 130, and more specifically the central protrusion 304, to be inserted at an angle up to twenty to thirty degrees of axis.

Referring now to FIG. 17, the collar 314 further includes an inner protruding annulus 327 and an outer protruding annulus 313. The inner protruding annulus 327 forms at least a portion of the collar inlet conduit 374 and is configured to interface and couple to the tube 174. The outer protruding annulus 313 is configured to surround and couple to reservoir opening 111. As previously discussed, in embodiments that utilize the O-ring 280, the O-ring 280 may seal against the outer surface of the reservoir opening 111. The O-ring 280 further seals against the inner surface of the outer protruding annulus 313. This ensures that saturated output air is funneled back up through the collar assembly 310 and not out between the collar assembly 310 and the reservoir 110.

The collar 314 further includes a collar exhaust aperture 317. The collar exhaust aperture 317 is a conduit that extends from the bottom of the collar 314 at a location between the inner protruding annulus 327 and the outer protruding annulus 313. The collar exhaust aperture 317 is a square or rectangular shaped aperture that funnels the saturated output exhaust from the reservoir 110 out and through a collar exhaust channel 332.

The collar exhaust channel 332 is a channel extending in a circular path in around the collar inlet conduit 374. The collar exhaust channel 332 extends from the collar exhaust aperture 317 to the opposite side of the collar inlet conduit 374 to allow saturated output exhaust to exit through a collar exhaust port 312 (see, for example, FIG. 17). The collar exhaust port 312 is an aperture formed by coupling the channel cap 320 to the collar 314. The channel cap 320 sits on a ledge to seal against the collar 314 and form an output conduit for the saturated output exhaust. The channel cap 320 may be attached or coupled to the collar 314 in various manners including, but not limited to, adhesives, mechanical interference fit, ultrasonic welding, etc.

The channel cap 320 includes a circular ring 321 with a central aperture 324, an inner protruding ledge 322, and an outer protruding ledge 323. The inner protruding ledge 322 is configured to cover the collar exhaust aperture 317. The outer protruding ledge 323 is configured to extend out and form the upper surface of the collar exhaust port 312.

The collar assembly 310 is configured to prevent spills. The collar exhaust aperture 317 and collar exhaust channel 332 prevent spills. Any essential oil that makes its way to the collar exhaust aperture 317 when the bottle is tipped must pass completely around the collar inlet conduit 374 before exiting the collar exhaust port 312. Surface tension inside of the small passageway helps to impede flow of essential oil as well.

The collar assembly 310 is configured to align the collar exhaust port 312 with the exhaust opening 146 of the cap 140. All together an exhaust passageway is formed that begins at the collar exhaust aperture 317 extends through the collar exhaust channel 332 and the collar exhaust port 312 and out the exhaust opening 146.

The collar 314 further includes locating notches 315 which cooperatively receive the locating knobs 305 of the engine mount. In addition, the collar 314 includes a shelf ledge 367 on which the cap 140 rests. The collar 314 further includes a cable notch 319 which, similar the cable slot 309 of the engine mount 300, permits USB cable 204 to pass between the collar assembly 310 and the cap 140.

Referring to FIGS. 17 and 19, the diffusing apparatus includes a tube 174. The tube 174 is pipe or conduit that funnels inlet air down the internal cavity 163 (see, for example, FIG. 25) of the reservoir 110 to a location near the bottom of the internal cavity 163, a location which is immersed in the essential oils. The formation of microbubbles through a diffuser tip 180 occur at the bottom of the reservoir 110 and bubble up the reservoir causing the air within the reservoir to saturate with the essential oils and exit through the exhaust passageway as previous described. The tube 174 is a circular pipe but other shapes are contemplated herein.

The tube 174 includes a side aperture 175. The side aperture 175 is a bypass vent hole on one side of the tube 174 extending from inside the tube 174 to the one side of the tube 174 (see, for example, FIG. 19). The side aperture 175 is small. In some embodiments, the side aperture 175 is less than one millimeter in diameter. In some embodiments, the side aperture 175 is 0.4 millimeters in diameter. The side aperture 175 is located between one-half and two-thirds of the height of the tube 174.

The side aperture 175 is configured to bypass a portion of the pressurized air flow that is channeling down the tube 174. The bypass portion is forced out the side aperture 175. The bypass portion is further configured to cut or break the bubbles that are being forced up the internal cavity 163 of the reservoir 110. By breaking the bubbles, the bypass portion exiting the side aperture 175 prevents or reduces bubble overflow into the exhaust passageway. Such a configuration allows the micro air pump unit 290 to operate continuously and at higher air flow rates.

In addition, as the essential oils deplete in the reservoir 110, the head pressure or the pressure at the bottom of the tube 174 decreases. As the head pressure decreases more air will exit at the bottom of the tube 174 while bypassing less air at the side aperture 175. The increased airflow at the bottom of the tube 174 will maintain performance of the diffusing apparatus 100 even at lower levels of essential oils in the reservoir 110. Furthermore, the bypass of some of the pressurized air through the side aperture 175 results in the essential oil reservoir lasting longer, improving overall efficiency of the diffusing apparatus. This is because not all of the pressurized air must pass through the bottom of the tube 174 into the essential oils, resulting in a longer reservoir life, but maintaining saturated exhaust velocity and projection of the aroma into the occupied room or space.

The tube 174 may be made of various materials. In some embodiments, the tube 174 is made of machined plastic. In some implementations, the tube 174 is formed or machined of polytetrafluoroethylene (PTFE). Dimensional stability of the side aperture 175 enables more consistent operation of the diffusing apparatus.

Positioned at the bottom of the tube 174 is the diffuser tip 180. Referring now to FIGS. 17 and 20-24, the diffuser tip 180 includes a central conduit 481. The bottom of the tube 174 interfaces and couples to the central conduit 481 of the diffuser tip 180. The pressurized air is forced down the central conduit 481 to the bottom of the diffuser tip 180 and out a plurality of orifices 482. The orifices 482 are recessed in from the outer surface 483 of the diffuser tip 180.

The diffuser tip 180 includes a bottom plate 485, orifice sidewalls 486, and the central conduit 481. The orifices 482 are a recessed channel formed between a bottom edge 488 of the central conduit 481, the orifice sidewalls 486, and an outer edge 489 of the bottom plate 485. The recessed orifices 482 form bubbles along the recessed channel which are then expelled from the diffuser tip 180 and forced up the reservoir 110. The size and number of orifices 482 may vary. In some embodiments, the diffuser tip 180 includes eight orifices 482 equally spaced around a perimeter of the base of the diffuser tip 180. The size, number, and shape of the orifices can be tuned to yield bubbles of an optimized size. Optimal bubble size formation allows for quiet formation of bubbles and helps prevent bubble overflow.

In some embodiments, the diffusing apparatus 100 further includes an electronic tilt sensor. The electronic tilt sensor is configured to sense if the diffusing apparatus 100 has been tipped over. The electronic tilt sensor is configured to signal printed circuit board controller 131 or the printed circuit board base controller 224 to turn off the micro air pump unit 290. In an example, the electronic tilt sensor is a 2-axis electronic Micro Electro Mechanical System (MEMS) accelerometer type integrated chip sensor. Other types of tilt sensors are contemplated but not described herein for the sake of brevity. The tilt sensor may be part of the base 220 or the controller assembly 130.

Figure 27:
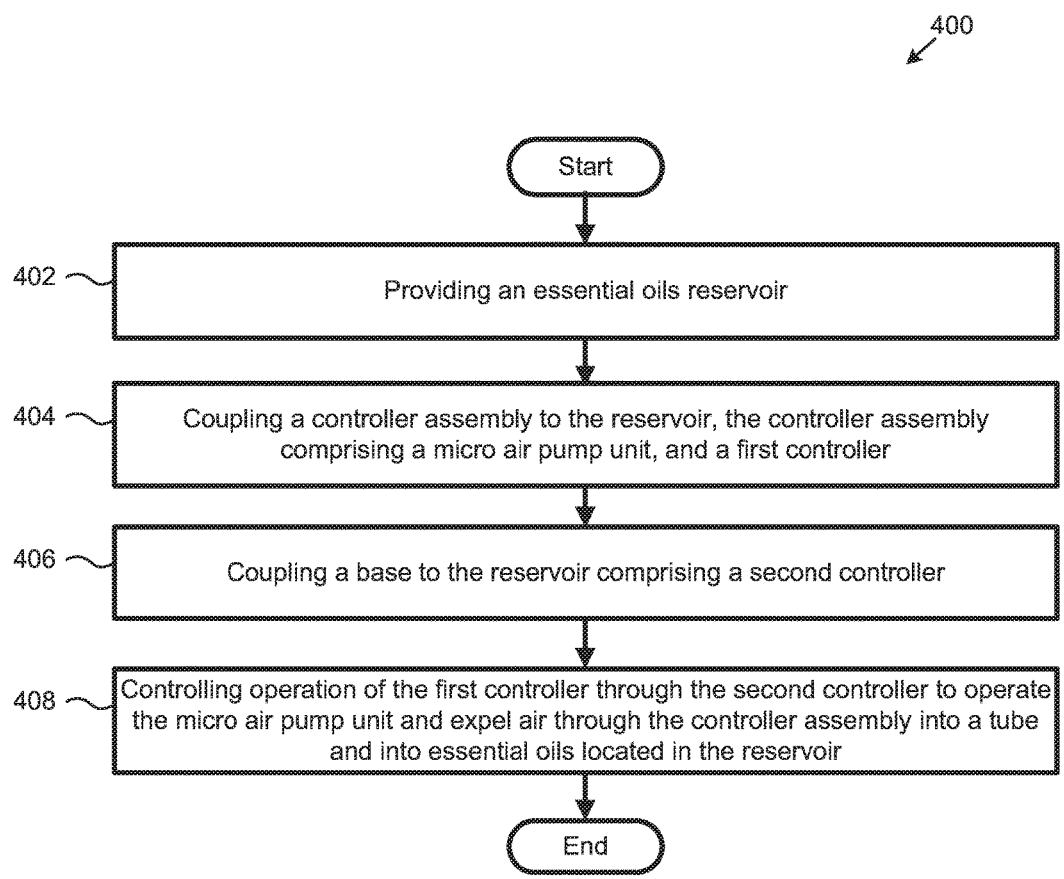
FIG. 27 is a schematic flow chart of a method of infusing air with essential oils, according to one or more embodiments of the present disclosure.

Now referring to FIG. 27, one embodiment of a method 400 of infusing air with essential oils is shown. The method 400 includes providing an essential oils reservoir at 402 and coupling a controller assembly to the reservoir, the controller assembly including a micro air pump unit, and a first controller at 404. At 406, the method 400 includes coupling a base to the reservoir comprising a second controller. At 408, the method 400 includes controlling operation of the first controller through the second controller to operate the micro air pump unit and expel air through the controller assembly into a tube and into essential oils located in the reservoir. The method then ends.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The schematic flow chart diagram included herein is generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A diffusing apparatus for diffusing essential oils into the air, the apparatus comprising:
    a reservoir configured to hold essential oils in an internal cavity;
    a controller assembly removably coupled to the reservoir, the controller assembly comprising an air inlet port, a first controller, and a micro air pump unit;
    a base communicably connected to the controller assembly, the base comprising a second controller, wherein the second controller is communicably connected to the first controller; and
    a tube in fluid connection at a first end with the micro air pump unit and extending into the reservoir, the tube providing a path for pressurized air from the micro air pump unit into the reservoir through a plurality of orifices at a second end of the tube.

2. The apparatus of claim 1, wherein:
    the base further comprises a rechargeable battery; and
    the rechargeable battery is configured to power the first controller.

3. The apparatus of claim 2, further comprising a plurality of LEDs in the base configured to illuminate the reservoir.

4. The apparatus of claim 1, wherein the micro air pump unit generates at least five hundred pascals of pressure.

5. The apparatus of claim 1, wherein the micro air pump unit consumes less than one Watt of power when operating.

6. The apparatus of claim 1, wherein the micro air pump unit produces airflow of up to one liter per minute.

7. The apparatus of claim 1, further comprising a collar assembly, wherein the controller assembly is removably coupled to the collar assembly and the collar assembly is removably coupled to the reservoir and to the tube.

8. The apparatus of claim 7, wherein the collar assembly comprises an exhaust passageway fluidly connecting the internal cavity of the reservoir with an exhaust opening on the controller assembly.

9. The apparatus of claim 8, wherein the collar assembly comprises a collar inlet port, a collar exhaust aperture, and a collar exhaust channel.

10. The apparatus of claim 9, wherein:
    the collar exhaust aperture is located on a first side of the collar inlet port; and
    the collar exhaust channel is a passageway extending from the first side of the collar inlet port and around the collar inlet port to a second side of the collar inlet port and out a side of the collar assembly.

11. The apparatus of claim 8, wherein the controller assembly includes a tilt sensor.

12. The apparatus of claim 1, wherein:
    the apparatus further includes a diffuser tip connected to the end of the tube below the oil level in the reservoir body; and
    the plurality of orifices are located on the diffuser tip.

13. The apparatus of claim 11, wherein the plurality of orifices in the diffuser tip are recessed into the diffuser tip from an outer surface of the diffuser tip.

14. The apparatus of claim 1, wherein the air inlet port comprises an angled channel, and wherein the controller assembly and the base are electronically connected through a serial communication cable and wherein the controller assembly and the base are configured to permit bi-directional communication.

15. The apparatus of claim 1, wherein the base comprises a first port configured to electronically connect to the controller assembly and a second port configured to electronically connect to an external device.

16. The apparatus of claim 1, wherein the second controller is configured to control the first controller, and wherein the second controller is configured to receive wireless communication from a remote computing device.

17. The apparatus of claim 1, wherein the tube further comprises a side aperture in a wall of the tube, wherein the side aperture is located at least one-half a height of the tube.

18. An apparatus for infusing air with essential oils, the device comprising:
- a reservoir configured to hold essential oils in an internal cavity;
- a controller assembly removably coupled to the reservoir, the controller assembly comprising an air inlet port, a first controller, and a micro air pump unit;
- a base communicably connected to the controller assembly, the base comprising a second controller, wherein the second controller is communicably connected to the first controller; and
- a tube in fluid connection at a first end with the micro air pump unit and extending into the reservoir, the tube providing a path for pressurized air from the micro air pump unit into the reservoir through a plurality of orifices at a second end of the tube, wherein the micro air pump unit generates at least five hundred pascals of pressure, and wherein the micro air pump unit consumes less than one Watt of power when generating the at least five hundred pascals.

19. The apparatus of claim 17, wherein the micro air pump unit is a piezoelectric diaphragm micro pump.

20. The apparatus of claim 17, wherein:
- the apparatus further comprises a collar assembly;
- the controller assembly is coupled to the collar assembly and the collar assembly is coupled to the reservoir and to the tube;
- the collar assembly comprises an exhaust passageway fluidly connecting the internal cavity of the reservoir with an exhaust opening on the controller assembly;
- the collar assembly comprises a collar inlet port, a collar exhaust aperture, and a collar exhaust channel;
- the collar exhaust aperture is located on a first side of the collar inlet port; and
- the collar exhaust channel is a passageway extending from the first side of the collar inlet port and around the collar inlet port to a second side of the collar inlet port and out a side of the collar assembly.

21. A method of infusing air with essential oils, the method comprising:
- providing an essential oils reservoir comprising a tapered internal cavity;
- coupling a controller assembly to the reservoir, the controller assembly comprising a micro air pump unit, and a first controller;
- coupling a base to the reservoir comprising a second controller; and
- controlling operation of the first controller through the second controller to operate the micro air pump unit and expel air through the controller assembly into a tube and into essential oils located in the reservoir.

* * * * *